(12) United States Patent
Repine

(10) Patent No.: US 7,026,313 B2
(45) Date of Patent: Apr. 11, 2006

(54) 2-THIA-1,6,8-TRIAZA-NAPHTHALENE-2,2-DIOXIDES ARE KINASE INHIBITORS

(75) Inventor: Joseph Thomas Repine, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 74 days.

(21) Appl. No.: 10/348,889

(22) Filed: Jan. 21, 2003

(65) Prior Publication Data
US 2003/0186973 A1  Oct. 2, 2003

Related U.S. Application Data

(60) Provisional application No. 60/350,758, filed on Jan. 22, 2002.

(51) Int. Cl.
C07D 513/04 (2006.01)
A61K 31/542 (2006.01)
(52) U.S. Cl. .................. 514/226.5; 544/48
(58) Field of Classification Search ............. 544/48; 514/226.5
See application file for complete search history.

(56) References Cited

FOREIGN PATENT DOCUMENTS

WO    WO 02/076463    * 10/2002

* cited by examiner

Primary Examiner—Bruck Kifle
(74) Attorney, Agent, or Firm—Bryan C. Zielinski; Galina M. Yakovleva

(57) ABSTRACT

The present invention provides 2-thia-1,6,8-triaza-naphthalene-2,2-dioxide inhibitors of cyclin-dependent kinases, uses thereof and pharmaceutical compositions thereof.

These compounds are useful for treating cell proliferative disorders, such as cancer, atherosclerosis, and restenosis. These compounds are potent inhibitors of kinases such as cyclin-dependent (cdks) and growth factor-mediated kinases.

The present invention also provides a method of treating cell proliferative disorders

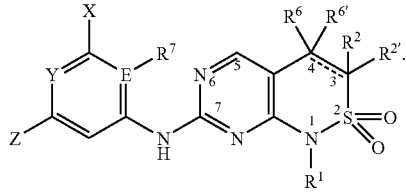

7 Claims, No Drawings

2-THIA-1,6,8-TRIAZA-NAPHTHALENE-2,2-DIOXIDES ARE KINASE INHIBITORS

This application claims the benefit of U.S. Patent Application No. 60/350,758 filed Jan. 22, 2002; the entire contents of which is hereby incorporated herein by reference.

FIELD OF THE INVENTION

This invention relates to 2-Thia-1,6,8-Triaza-Naphthalene-2,2-Dioxides as inhibitors of kinases, particularly cyclin-dependent kinases. The compounds of the invention are useful for the treatment of inflammation, cell proliferative diseases such as cancer and restenosis, and neurodegenerative diseases such as Alzheimer's disease.

SUMMARY OF THE RELATED ART

Cyclin-dependent kinases and related serine/threonine protein kinases are important cellular enzymes that perform essential functions in regulating cell division and proliferation. The cyclin-dependent kinase catalytic units, of which nine have now been described, are activated by regulatory subunits known as cyclins. At least 16 mammalian cyclins have been identified (Johnson, D. G. & Walker, C. L. Annu. Rev. Pharmacol. Toxicol 1999, 39, 295–312). Cyclin D/Cdk4, Cyclin D/Cdk6, CyclinB/Cdk1, Cyclin A/cdk2 and Cyclin E/cdk2 are all important regulators of cell cycle progression. Other functions of cyclin/Cdk heterodimers include regulation of transcription, DNA repair, differentiation and apoptosis. Increased activity or temporally abnormal activation of certain of these kinases has been shown to result in the development of human tumors and other proliferative disorders such as restenosis. Indeed, human tumor development is commonly associated with alterations in either the Cdk proteins themselves or their regulators (Cordon-Cardo, C. Am. J. Pathol. 1995, 147, 545–560; Karp, J. E. & Broder, S. Nat. Med. 1995, 1, 309–320; Hall, M. et al. Adv. Cancer Res. 1996, 68, 67–108; Sher, C. J. Science, 1996, 274, 1672–1677). This observation has prompted an intensive search for small molecule CDK inhibitors.

Inhibitors of Cdk enzymes may be expected to inhibit uncontrolled cell proliferation (D. W. Fry & M. D. Garrett, Curr. Opin. Endocrine, Metabolic Invet. Drugs, 2000, 2, 40–59.). Indeed, naturally occurring protein inhibitors of Cdks appear to perform this function providing strong validation for this approach. Introduction of p16 into lung cancer cell lines blocked entry into S phase and caused growth inhibition (Jin, X. et al. Cancer Res. 1995, 55, 3250–3253; Chintaia, S. K. et al. Oncogene 1997, 15, 2049–2057). Other studies have demonstrated a similar effect for p27 Craig, C. et al. Oncogene 1997, 14, 2283–2289). Growth inhibition also results from expression of antisense cyclin D1 or Dominant negative (DN) cdk2.

In addition to treating cancer, Cdk inhibitors also may have potential applications in the treatment of cardiovascular disorders such as restenosis and atherosclerosis. Vascular smooth muscle proliferation and intimal hyperplasia following balloon angioplasty are inhibited by over-expression of the cyclin-dependent kinase inhibitor protein p21 (Chang, M. W. et al. J. Clin. Invest, 1995, 96, 2260; Yang, Z-Y. et al. Proc. Natl. Acad. Sci(USA) 1996, 93, 9905). Moreover, intraluminal exposure of a denuded rat carotid artery to the purine cdk2 inhibitor CVT-313 (Ki=95 nM) resulted in greater than 80% inhibition of neointima formation. Taken together, these observations support the use of small molecule inhibitors of cell cycle progression in the treatment of vascular disorders that are due to aberrant cell proliferation.

The neuronal Cdc2-like kinase, known as Cdk5, together with its brain specific activator protein p35/p25, phosphorylates the neuron-specific microtubule-associated protein tau (Lew, J & Wang, J. H. Trends Biochem. Sci 1995, 20, 33). Aberrant expression of Cdk5 is proposed to contribute to the neurodegenerative disorder Multiple System Atrophy (Nakamura, S. et al. J. Neuropathol. Exp. Neurol. 1998, 57, 690). In addition, tau hyperphosphorylation has long been associated with the pathogenesis of Alzheimer's disease (AD) (Spillantini, M. G. & Giedert, M. Trends Neurosci. 1998, 21, 428–433). Cdk5 is an important therapeutic target because its activator protein p35 is specifically localized in central and peripheral neurons (Tsai, J.-H., et al. Nature 1984, 371, 419–423). Indeed the abnormal deposition of amyloid beta peptide (from the APP gene) and hyperphosphorylated tau may be combined factors that lead to early onset AD (Mandelkow, E. M. & Mandelkow, E. Trends Cell Biol. 8, 425–427). There is growing evidence that abnormally processed tau also is associated with other CNS diseases. Recently, mutations in the tau gene on chromosome 14 have been linked to fronto-temporal dementia with Parkinsonism (FTDP-17) and progressive supernuclear palsy (PSP) (Spillantini, M. G. & Giedert, M. Trends Neurosci. 1998, 21, 428–433).

Other diseases in which CDK inhibitors could find application include a variety of infections. For example, cyclin-dependent kinases are required for viral replication following infection by herpes simplex virus (HSV) (Schang, L. M. et al. J. Virol. 1998, 72, 5626). HSV replication was inhibited by the cyclin-dependent kinase inhibitors roscovitine and olomoucine but not by a cell cycle inhibitor that does not inhibit cyclin-dependent kinase activity. Inactivation of the Cdk inhibitor protein (CDI) p16$^{INK4A}$ by the viral protein Tax, or inactivation of the CDI p27 by viral E1A, has been demonstrated to overcome cell cycle suppression and promote cell immortalization and the transformed phenotype (Mal, A. et al. Nature 1996, 380, 262; Suzuki, T. et al. EMBO J. 1996, 15, 1607; Parker, G. A. et al. Oncogene 1996, 13, 2541). cdk2 has also been implicated in the progression of cytomegalovirus infections (Bresnahan, W. A. et al. Virology, 1997, 231, 239). Fungal infections may be expected to be susceptible to Cdk inhibitors on the basis of the known essential roles of Cdks analogs in yeast.

Due to the essential role of Cdks in the regulation of cell proliferation, Cdk inhibitors could potentially find application in a wide range of disorders including diseases and disorders of cellular proliferation such as fibroproliferative and differentiative disorders, vascular smooth cell proliferation, and cancer, including solid cancers and leukemias. Specific diseases that may be treated include: viral infections including DNA viruses such as herpes and RNA viruses such as HIV; fungal infections; neurodegenerative diseases including Alzheimer's disease; autoimmune diseases such as psoriasis, rheumatoid arthritis, lupus, type 1 diabetes and diabetic nephropathy, and multiple sclerosis; gomerulonephritis; polyposis; neuro-fibromatosis; pulmonary fibrosis; acute and chronic nephropathies; acute and chronic inflammation including inflammatory bowel disease; gout; polycystic kidney disease; benign prostatic hyperplasia; arterial restenosis, post-surgical stenosis and restenosis; atherosclerosis;hemangioma; atheroma; familial adenomatosis. In addition, Cdk inhibitors may be effective against diseases of angiogenesis, including ocular diseases with retinal vessel proliferation, and could find application against organ transplant rejection and host vs graft disease.

Cdk inhibitors are expected to be especially effective against cancer including: carcinoma of the bladder, breast, colon, kidney, liver, lung (including small cell lung cancer), esophagus, gall-bladder, ovary, pancreas, stomach, cervix, thyroid, prostate and skin (including squamous cell carcinoma); hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma, non-Burkett's lymphoma; Hematopoietic tumors of myeloid lineage, including acute and chronic myelogenous leukemias, myelodysplastic syndrome and promyelocytic leukemia; tumors of mesenchymal origin, including fibrosarcoma and rhabdosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratocanthoma, thyroid follicular cancer and Kaposi's sarcoma.

SUMMARY OF THE INVENTION

This invention provides 2-Thia-1,6,8-Triaza-Naphthalene-2,2-Dioxides that are useful for treating inflammation, cell proliferative diseases such as cancer and restenosis, and neurodegenerative diseases such as Alzheimer's disease. The compounds of the invention are selective inhibitors of Cdks. The compounds of the invention are readily synthesized, and can be administered to patients by a variety of methods.

The compounds of the invention are those having the structure of Formula I:

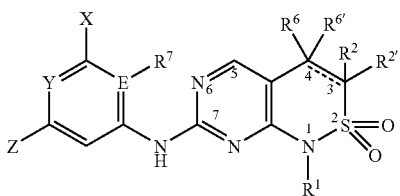

all stereoisomers of the above formula where saturated at C3 and C4, pharmaceutically acceptable salts, esters, amides, prodrugs thereof, wherein:
$R^1$ is hydrogen;
  lower alkyl optionally substituted with one, two, or three groups independently selected from halogen, hydroxy, lower alkoxy, amino, mono- or dialkylamino, carboxy, alkoxycarbonyl, thio alkyl, nitrile, aryl, heteroaryl, or a carbocyclic group containing from 3–7 members, up to two of which members are optionally heteroatoms independently selected from oxygen, sulfur, and nitrogen; or
  a carbocyclic group containing from 3–7 members, up to two of which members are optionally heteroatoms independently selected from oxygen, sulfur, and nitrogen, wherein the carbocyclic group is unsubstituted or substituted with one, two, or three groups independently selected from halogen, hydroxy, lower alkyl, lower alkoxy, amino, mono- or dialkylamino, aryl, and heteroaryl;
$R^2$ and $R^{2'}$ are independently hydrogen, lower alkyl, lower hydroxyalkyl, lower alkoxy, halogen, haloalkyl, lower alkynyl, lower alkenyl, nitrile, nitro, $C_3$–$C_7$ cycloalkyl, —$OR^3$, —$COR^3$, —$CO_2R^3$, —$CONR^3R^4$, —$SO_2NR^3R^4$, —$SO_2R^3$, —$NCOR^3R^4$, —$NSO_2R^3R^4$, or —$NR^3R^4$, —$(CR^3R^4)_mNR^8R^9$, —$(CR^3R^4)_mOR^8$, —$(CR^3R^4)_m$-aryl, —$(CR^3R^4)_m$-heteroaryl, -$T(CH_2)_mQR$, —$C(O)T(CH_2)_mQR^3$, —$NR^3C(O)T(CH_2)_mQR^4$, —$CR^3$=$CR^4C(O)R^8$, or —$SR^4$;
  wherein $R^{2'}$ is absent when the bond between C3 and C4 is a carbon-carbon double bond;
E is C or N; $R^7$ is hydrogen, halogen, lower alkyl, lower alkoxy, or alkylcarbonyl, provided that $R^7$ is absent when E is N;
Y is N or $CR^5$;
$R^6$ and $R^{6'}$ are independently hydrogen, hydroxy, lower alkyl, hydroxyalkyl or haloalkyl,
  wherein $R^{6'}$ is absent when the bond between C3 and C4 is a carbon-carbon double bond, or when $R^6$ is hydroxy, then $R^{6'}$=H
X and Z are independently hydrogen, halogen, lower alkyl, lower alkoxy, trifluoromethyl, hydroxy, nitrile, nitro, —$NR^3R^4$, —$N(O)R^3R^4$, —$SR^3$, —$C(O)R^3$, —$CO_2R^3$, —$CONR^3R^4$, —$SO_2NR^3R^4$, —$SO_2R^3$, -$T(CH_2)_mQR^3$, —$C(O)T(CH_2)_mQR^3$, or —$NR^3C(O)T(CH_2)_mQR^4$;
m is 0–6;
T is O, S, $NR^3$, $N(O)R^3$, or $CR^3R^4$;
Q is O, S, $NR^3$, $N(O)R^3$, or $CO_2$;
$R^5$ is $NR^3R^4$, $N(O)R^3R^4$, OH, $OR^3$, $SR^3$, halo, $COR^3$, $(CH_2)_mR^3$, $CO_2R^3$, $CONR^3R^4$, $S(O)_nR^3$, $SO_2R^3$, $SO_2NR^3R^4$, $NR^3SO_2R^4$, nitrile, nitro, alkyl, alkoxyalkyl, $T(CH_2)_mQR^3$, $C(O)T(CH_2)_mQR^3$, $NR^3C(O)T(CH_2)_mQR^4$, or $T(CH_2)_mCO_2R^3$;
Each of $R^3$ and $R^4$ are independently hydrogen, lower alkyl, lower alkenyl, lower alkynyl, $(CH_2)_mAr$, arylalkyl, aryl, heteroaryl, heteroarylalkyl, cycloalkyl, heterocycloalkyl, or heteroaryl, or $R^3$ and $R^4$ together with the nitrogen to which they are attached form a carbocyclic ring containing 3–8 members, up to four of which members are optionally carbonyl groups or heteroatoms independently selected from oxygen, sulfur, S(O), S(O)$_2$, and nitrogen, wherein the carbocyclic group is unsubstituted or substituted with one, two, three, or four groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylamino alkyl, amino, mono- or dialkylamino, N-hydroxyacetamido, aryl, heteroaryl, carboxyalkyl, —$NR^8SO_2R^9$, —$C(O)NR^8R^9$, —$NR^8C(O)R^9$, —$C(O)OR^8$, —$(CH_2)_mS(O)_nR^8$, —$(CH_2)_m$-heteroaryl, —$O(CH_2)_m$-heteroaryl, —$(CH_2)_mC(O)NR^8R^9$, or —$O(CH_2)_mC(O)OR^8$;
n is 0–2; and
Each of $R^8$ and $R^9$ are independently hydrogen, lower alkyl, lower alkenyl, lower alkynyl, $(CH_2)_mAr$, arylalkyl, aryl, heteroaryl, heteroarylalkyl, cycloalkyl, heterocycloalkyl, or heteroaryl.

The present invention also provides pharmaceutical compositions that comprise a compound of Formula I together with a pharmaceutically acceptable diluent, carrier, or excipient.

The present invention also provides methods for inhibiting cyclin-dependent kinase and growth factor-mediated kinase enzymes.

The present invention also provides a method of treating subjects suffering from diseases caused by cellular proliferation. The method entails inhibiting proliferation of tumorigenic cells of epithelial origin and vascular smooth muscle proliferation, and/or cellular migration by administering a therapeutically effective amount of a compound of Formulas I, II, III, IV and V to a subject in need of treatment.

The invention also provides compounds useful in the diagnosis and treatment of cancer, psoriasis, vascular smooth muscle cell proliferation associated with atherosclerosis and postsurgical vascular stenosis and restenosis in mammals.

The present invention also provides a method of treating subjects suffering from diseases caused by DNA tumor viruses such as herpes viruses.

DETAILED DESCRIPTION OF THE INVENTION

The novel compounds encompassed by the instant invention are 2-thia-1,6,8-triaza-naphthalene-2,2-dioxides described by the general Formula I,

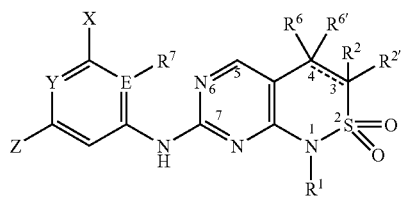

all stereoisomers of the above formula where saturated at C3 and C4, pharmaceutically acceptable salts, esters, amides, prodrugs thereof, wherein:

$R^1$ is hydrogen; lower alkyl optionally substituted with one, two, or three groups independently selected from halogen, hydroxy, lower alkoxy, amino, mono- or dialkylamino, carboxy, alkoxycarbonyl, thio alkyl, nitrile, aryl, heteroaryl, or a carbocyclic group containing from 3–7 members, up to two of which members are optionally heteroatoms independently selected from oxygen, sulfur, and nitrogen; or a carbocyclic group containing from 3–7 members, up to two of which members are optionally heteroatoms independently selected from oxygen, sulfur, and nitrogen, wherein the carbocyclic group is unsubstituted or substituted with one, two, or three groups independently selected from halogen, hydroxy, lower alkyl, lower alkoxy, amino, mono- or dialkylamino, aryl, and heteroaryl;

$R^2$ and $R^{2'}$ are independently hydrogen, lower alkyl, lower hydroxyalkyl, lower alkoxy, halogen, haloalkyl, lower alkynyl, lower alkenyl, nitrile, nitro, $C_3$–$C_7$ cycloalkyl, —$OR^3$, —$COR^3$, —$CO_2R^3$, —$CONR^3R^4$, —$SO_2NR^3R^4$, —$SO_2R^3$, —$NCOR^3R^4$, —$NSO_2R^3R^4$, —$NR^3R^4$, —$(CR^3R^4)_mNR^8R^9$, —$(CR^3R^4)_mOR^8$, —$(CR^3R^4)_m$-aryl, —$(CR^3R^4)_m$-heteroaryl, -$T(CH_2)_mQR$, —$C(O)T(CH_2)_mQR^3$, —$NR^3C(O)T(CH_2)_mQR^4$, —$CR^3$=$CR^4C(O)R^8$, or —$SR^4$;

wherein $R^{2'}$ is absent when the bond between C3 and C4 is a carbon-carbon double bond;

E is C or N; $R^7$ is hydrogen, halogen, lower alkyl, lower alkoxy, or alkylcarbonyl, provided that $R^7$ is absent when E is N;

Y is N or $CR^5$;

$R^6$ and $R^{6'}$ are independently hydrogen, hydroxy, lower alkyl, hydroxyalkyl or haloalkyl, wherein $R^{6'}$ is absent when the bond between C3 and C4 is a carbon-carbon double bond, or when $R^6$ is hydroxy, then $R^{6'}$=H;

X and Z are independently hydrogen, halogen, lower alkyl, lower alkoxy, trifluoromethyl, hydroxy, nitrile, nitro, —$NR^3R^4$, —$N(O)R^3R^4$, —$SR^3$, —$C(O)R^3$, —$CO_2R^3$, —$CONR^3R^4$, —$SO_2NR^3R^4$, —$SO_2R^3$, -$T(CH_2)_mQR^3$, —$C(O)T(CH_2)_mQR^3$, or —$NR^3C(O)T(CH_2)_mQR^4$;

m is 0–6;

T is O, S, $NR^3$, $N(O)R^3$, or $CR^3R^4$;

Q is O, S, $NR^3$, $N(O)R^3$, or $CO_2$;

$R^5$ is $NR^3R^4$, $N(O)R^3R^4$, OH, $OR^3$, $SR^3$, halo, $COR^3$, $(CH_2)_mR^3$, $CO_2R^3$, $CONR^3R^4$, $S(O)_nR^3$, $SO_2R^3$, $SO_2NR^3R^4$, $NR^3SO_2R^4$, nitrile, nitro, alkyl, alkoxyalkyl, $T(CH_2)_mQR^3$, $C(O)T(CH_2)_mQR^3$, $NR^3C(O)T(CH_2)_mQR^4$, or $T(CH_2)_mCO_2R^3$;

n is 0–2;

Each of $R^3$ and $R^4$ are independently hydrogen, lower alkyl, lower alkenyl, lower alkynyl, $(CH_2)_mAr$, arylalkyl, aryl, heteroaryl, heteroarylalkyl, cycloalkyl, heterocycloalkyl, or heteroaryl, or $R^3$ and $R^4$ together with the nitrogen to which they are attached form a carbocyclic ring containing 3–8 members, up to four of which members are optionally carbonyl groups or heteroatoms independently selected from oxygen, sulfur, S(O), S(O)$_2$, and nitrogen, wherein the carbocyclic group is unsubstituted or substituted with one, two, three, or four groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, mono- or dialkylamino, N-hydroxyacetamido, aryl, heteroaryl, carboxyalkyl, —$NR^8SO_2R^9$, —$C(O)NR^8R^9$, —$NR^8C(O)R^9$, —$C(O)OR^8$, —$(CH_2)_mS(O)_nR^8$, —$(CH_2)_m$-heteroaryl, —$O(CH_2)_m$-heteroaryl, —$(CH_2)_mC(O)NR^8R^9$, or —$O(CH_2)_mC(O)OR^8$;

Each of $R^8$ and $R^9$ are independently hydrogen, lower alkyl, lower alkenyl, lower alkynyl, $(CH_2)_mAr$, arylalkyl, aryl, heteroaryl, heteroarylalkyl, cycloalkyl, heterocycloalkyl, or heteroaryl; and the pharmaceutically acceptable salts, esters, amides, and prodrugs thereof.

In addition to the compounds of Formula I, the invention encompasses, in a preferred embodiment, compounds of Formula II:

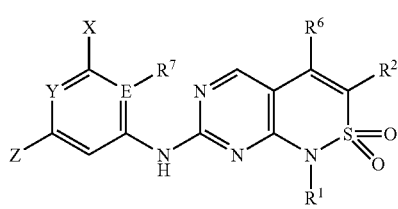

wherein E, X, Y, Z, $R^1$, $R^2$, $R^6$, $R^7$, $R^8$ and $R^9$ are as defined above for Formula I.

Preferred compounds of Formula II are those in which X and Z are independently hydrogen, Cl, or F; Y is $CR^5$;

E is C,

R$^7$ is H,

R$^2$ is hydrogen, Br, or alkyl;

R$^6$ is hydrogen or methyl.

R$^1$ is isopropyl, cyclohexyl or cyclopentyl.

In addition, the present invention also encompasses preferred compounds of the Formula III:

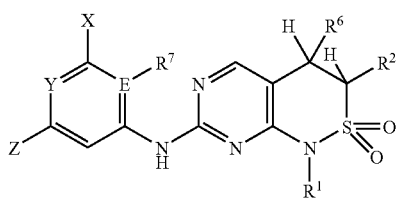

III wherein E, X, Y, Z, R$^1$, R$^2$, R$^6$, R$^7$, R$^8$ and R$^9$ are as defined above for Formula I.

Preferred compounds of Formula III are those in which X and Z are independently hydrogen, Cl, or F; Y is CR$^5$;

E is C,

R$^7$ is H,

R$^2$ is hydrogen or alkyl;

R$^6$ is hydrogen or methyl.

R$^1$ is isopropyl, cyclohexyl or cyclopentyl.

In addition, the present invention also encompasses, as a further preferred embodiment, compounds of the Formula IV:

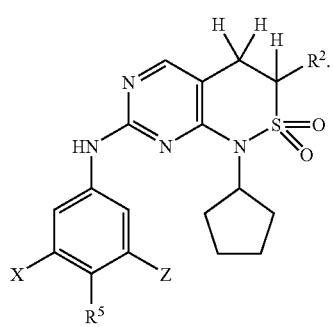

IV

More Preferred compounds of Formula IV are those wherein:

R$^2$ is hydrogen or methyl;

X and Z independently are hydrogen or halogen;

R$^5$ is NR$^3$R$^4$; and

R$^3$ and R$^4$ taken together with the nitrogen to which they are attached may form a 5- or 6-membered carbocyclic ring, optionally containing an oxygen, or nitrogen heteroatom, and optionally substituted with amino, alkyl or substituted alkyl groups.

The most preferred invention compounds have the Formula V

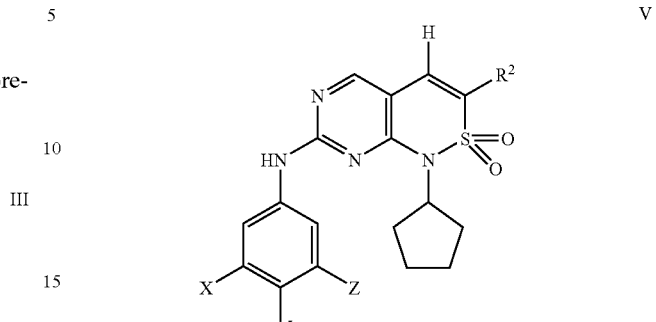

V wherein:

R$^2$ is hydrogen or C$_1$–C$_6$ alkyl;

X and Z independently are hydrogen or halogen;

R$^5$ is NR$^3$R$^4$; and

R$^3$ and R$^4$ taken together with the nitrogen to which they are attached may form a 5- or 6-membered carbocyclic ring, optionally containing an oxygen or nitrogen heteroatom, and optionally substituted with alkyl or substituted alkyl groups.

Unless otherwise expressly stated, the following definitions are adhered to throughout this disclosure.

By "alkyl," "lower alkyl," and "C$_1$–C$_6$ alkyl" in the present invention is meant a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, iso-pentyl, n-hexyl, and the like.

By the term "halogen" in the present invention is meant fluorine, bromine, chlorine, and iodine.

"Alkenyl" means straight or branched hydrocarbon radicals having from 2 to 6 carbon atoms and at least one double bond and includes ethenyl, 3-buten-1-yl, 2-ethenylbutyl, 3-hexen-1-yl, and the like.

"Alkynyl" means straight or branched hydrocarbon radicals having from 2 to 6 carbon atoms and at least one triple bond and includes ethenyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, amino, alkyl, and dialkylamino, and the like. Also included are rings in which 1 to 3 heteroatoms replace carbons. Such groups are termed "heterocyclic," which means a cycloalkyl group also bearing at least one heteroatom selected from O, S, or N, examples being oxiranyl, piperazinyl, pyrrolidinyl, piperidyl, tetrahydropyran, and morpholine.

By "alkoxy," "lower alkoxy," and "C$_1$–C$_6$ alkoxy" is meant straight or branched chain alkoxy groups having 1–10 carbon atoms, such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, and 3-methylpentoxy. In addition, alkoxy refers to polyethers such as —O—(CH$_2$)$_2$—O—CH$_3$, and the like.

"Acyl" means an alkyl or aryl (Ar) group bonded through a carbonyl group, i.e., R—C(O)—. For example, acyl includes a $C_1$–$C_6$ alkanoyl, including substituted alkanoyl, wherein the alkyl portion can be substituted by $NR^3R^4$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^3R^4$, phenyl, substituted phenyl, thio $C_1$–$C_6$ alkyl, $C_1$–$C_6$ alkoxy, hydroxy, carboxy, $C_1$–$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph where n is 1, 2, or 3. Perhalo and polyhalo substitution is also included.

Examples of substituted alkyl groups include 2-aminoethyl, 2-hydroxyethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanylethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, triazolyl, imidazolyl, (is)oxazolyl, oxadiazolyl, tetrazolyl, pyridyl, thiadiazolyl, oxadiazolyl, oxathiadiazolyl, thiatriazolyl, pyrimidinyl, (iso)quinolinyl, napthyridinyl, phthalimidyl, benzimidazolyl, and benzoxazolyl. A preferred heteroaryl is pyridine.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can be mono-, di-, or trisubstituted with, e.g., halogen, lower alkyl, lower alkoxy, lower alkylthio, trifluoromethyl, lower acyloxy, aryl, heteroaryl, and hydroxy. A preferred aryl is phenyl.

The term "cancer" includes, but is not limited to, the following cancers: cancers of the breast, ovary, cervix, prostate, testis, esophagus, glioblastoma, neuroblastoma, stomach, skin, bone, colon, pancreas, thyroid, buccal cavity and pharynx (oral), lip, tongue, mouth, pharynx, small intestine, colon-rectum, large intestine, rectum, brain and central nervous system, or lung, keratoacanthoma, epidermoid carcinoma, large cell carcinoma, adenocarcinoma, adenocarcinoma, adenoma, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, and leukemia.

The term "all stereoisomers at C3 and C4 and pharmaceutically acceptable salts, esters, amides, and prodrugs" as used herein refers to all stereoisomers of carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.*, 1977;66: 1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

Representative compounds of the invention are shown below in Table 1.
TABLE 1
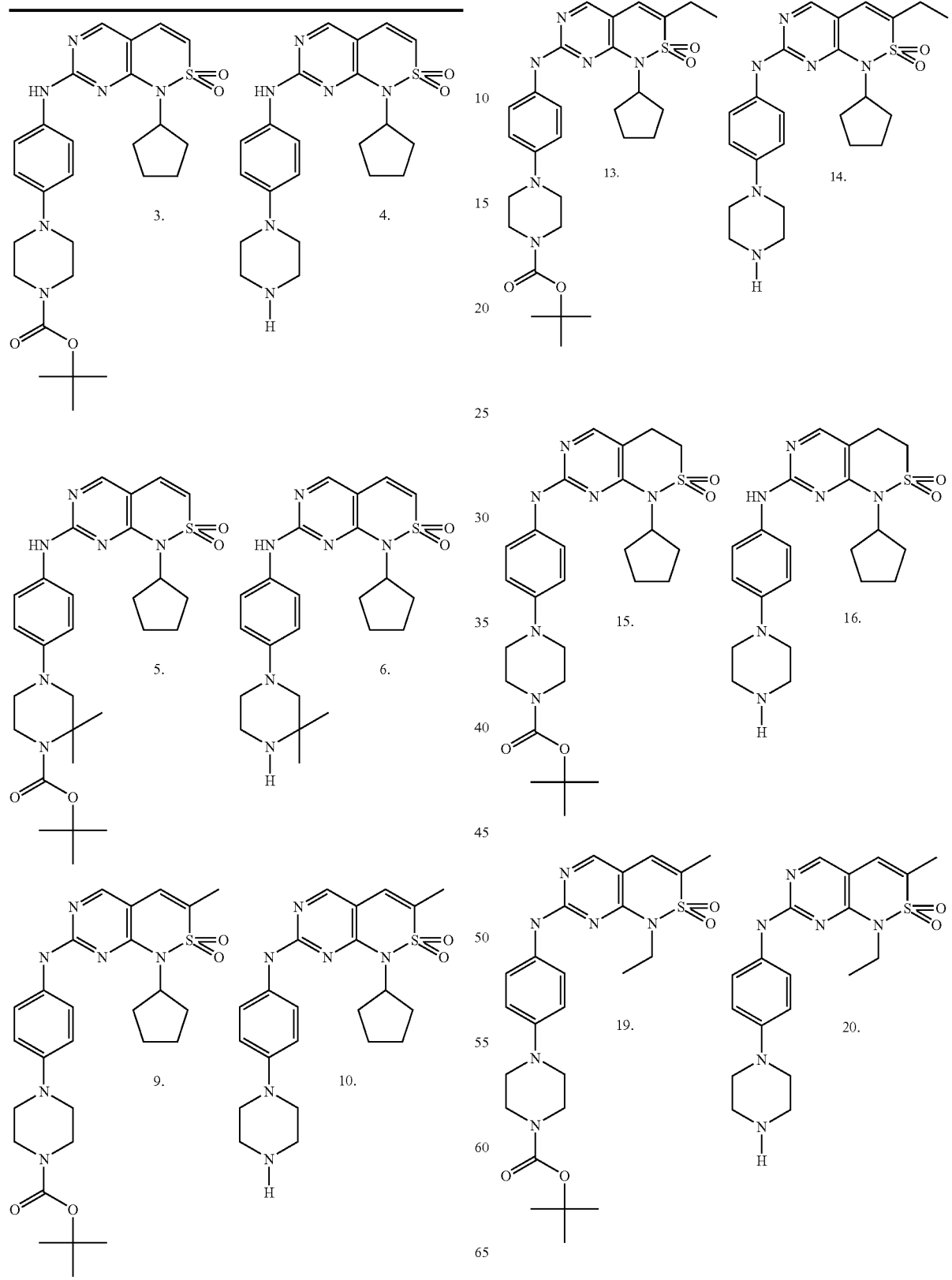
TABLE 1-continued TABLE 1-continued
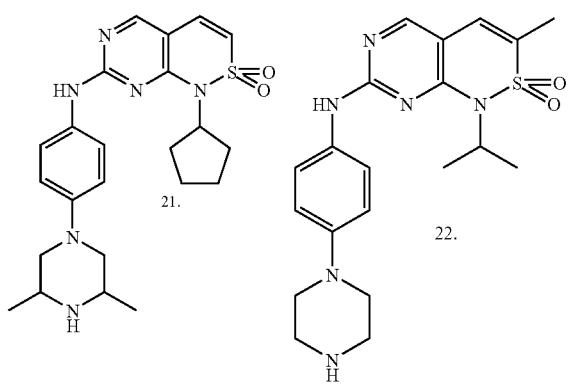
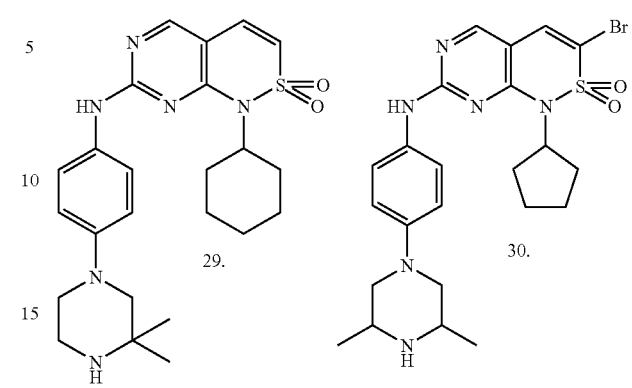
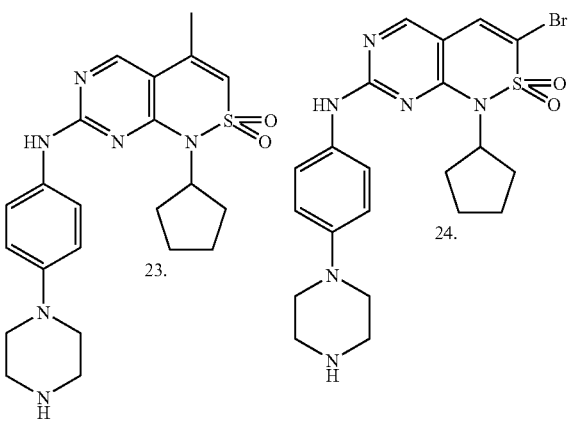
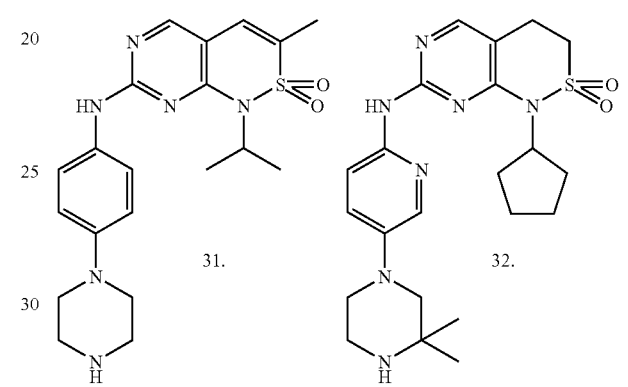
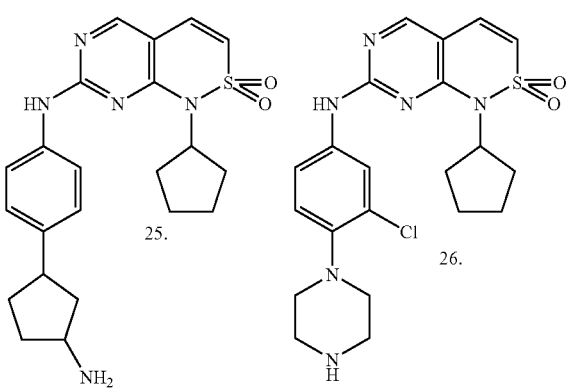
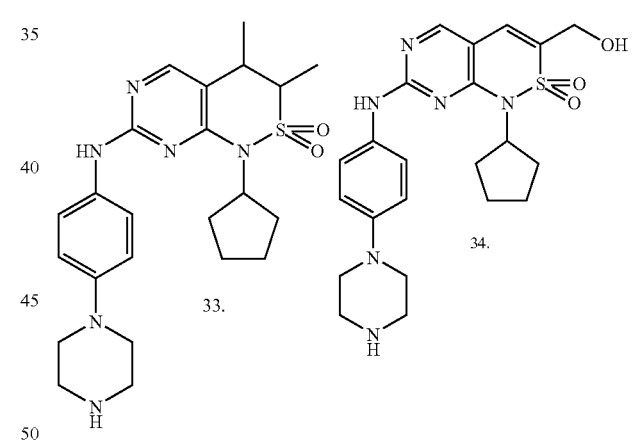
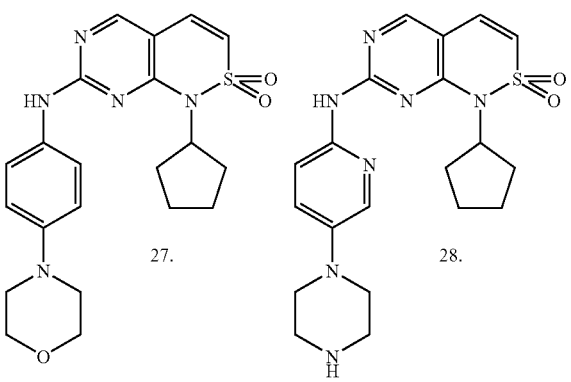
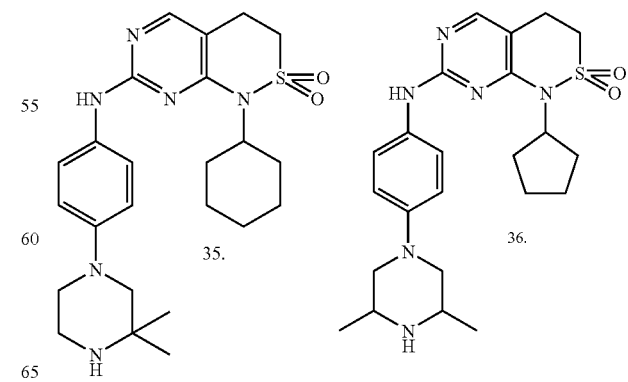

TABLE 1-continued

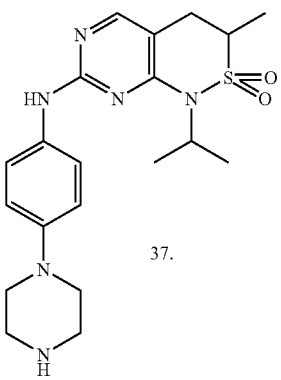

37.

Representative compounds of the present invention, which are encompassed by Formula I, include, but are not limited to the compounds in Table 1 and their pharmaceutically acceptable acid or base addition salts, or amide or prodrugs thereof.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming both pharmaceutically acceptable formulations comprising salts, including but not limited to acid addition and/or base salts, solvents and N-oxides of a compound of Formula I. This invention also provides pharmaceutical formulations comprising a compound of Formula I together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science,* 1977;66: 1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

This invention also provides pharmaceutical formulations comprising any or all stereoisomers of the compound of Formula I as well as mixtures of the stereoisomers. All of these forms are contemplated within the present invention.

The compounds of the present invention are useful for treating cancer (for example, leukemia and cancer of the lung, breast, prostate, and skin such as melanoma) and other proliferative diseases including but not limited to psoriasis, HSV, HIV, restenosis, and atherosclerosis. To utilize a compound of the present invention to treat cancer, a patient having cancer is administered a therapeutically effective amount of a pharmaceutically acceptable composition comprising an invention compound.

A further embodiment of this invention is a method of treating subjects suffering from diseases caused by vascular smooth muscle cell proliferation. Compounds within the scope of the present invention effectively inhibit vascular smooth muscle cell proliferation and migration. The method entails inhibiting vascular smooth muscle proliferation, and/or migration by administering an effective amount of a compound of Formula I to a subject in need of treatment.

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

A further embodiment of this invention is a pharmaceutical formulation comprising a compound of Formula I together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose of a compound of Formula I will generally be from about 1 mg to about 100 mg/kg of body weight per day. Typical adult doses will be about 50 mg to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I is administered a dosage of about 1 to about 500 mg per day, either singly or in multiple doses over a 24-hour period. This treatment may be repeated at subsequent intervals as needed.

The compounds of the present invention are capable of binding to and inhibiting the activity of proteins having the ability to phosphorylate other proteins, such as cdks, PDGFr, FGFr, c-Src, and EGFr-FL. Cdks form complexes with cyclins, and these complexes phosphorylate key proteins allowing cells to proceed through the cell cycle (Meijer L., *Progress in Cell Cycle Research,* 1995;1:351–363). The compounds of this invention inhibit this phosphorylation and therefore can be used as anti-proliferative agents for the treatment of cancer and/or restenosis and other proliferative diseases.

Because of their inhibitory activity against cdks and other kinases, the compounds of the present invention are also useful research tools for studying the mechanism of action of those kinases, both in vitro and in vivo.

The examples presented below are intended to illustrate particular embodiments of the invention, and are not intended to limit the scope of the specification or the claims in any way.

An illustration of the preparation of compounds of the present invention is shown in Schemes 1, 2 and 3 below. One of skill in the art will recognize that other preparative methods may also be utilized.

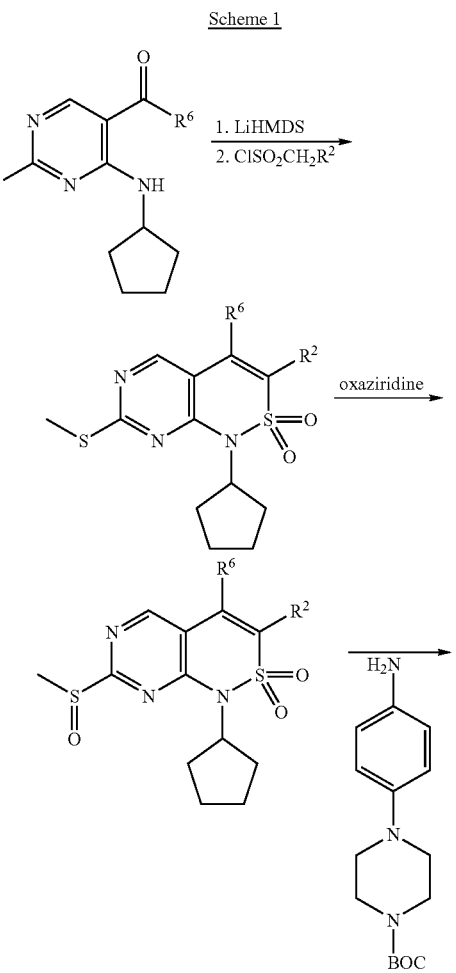

Scheme 1

19
-continued
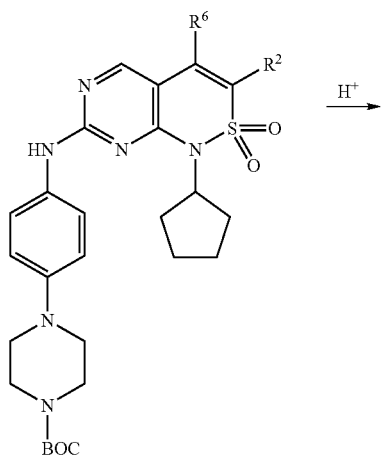
20
-continued
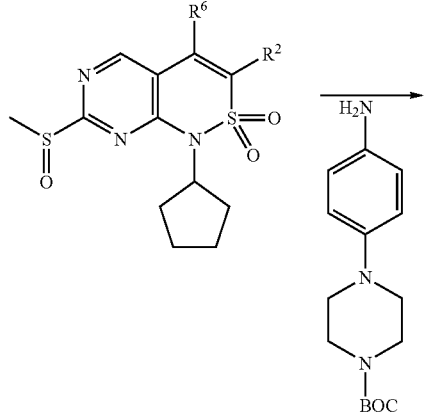
Scheme 2
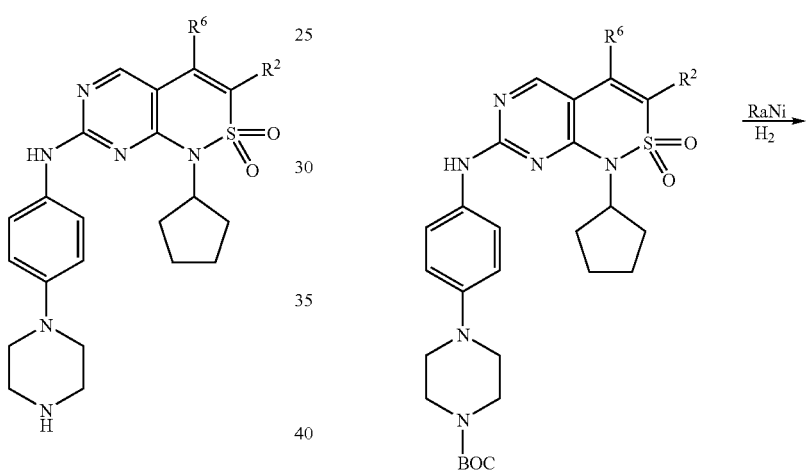
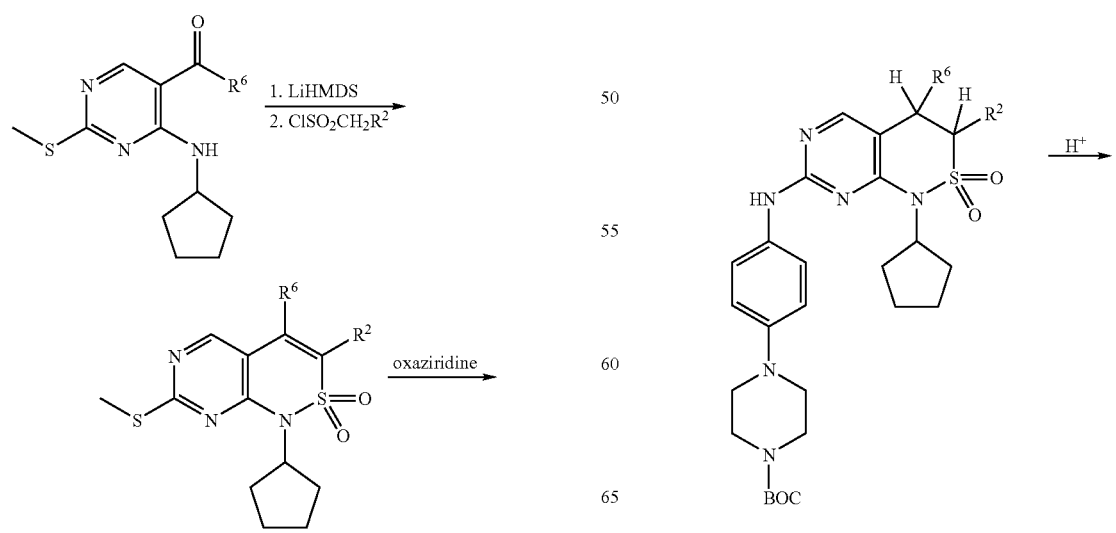

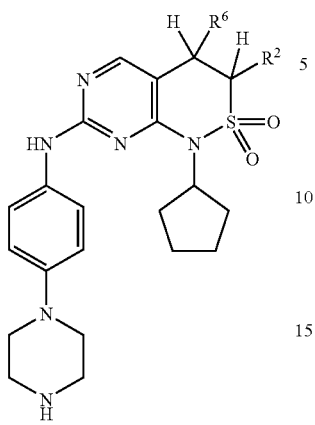
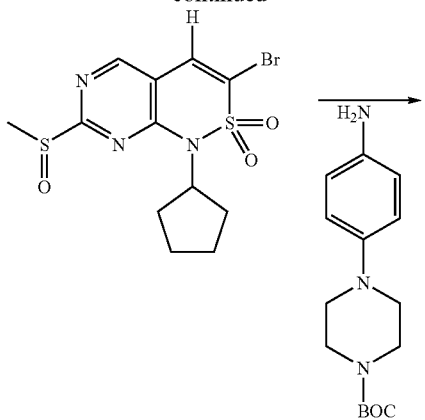
Scheme 3
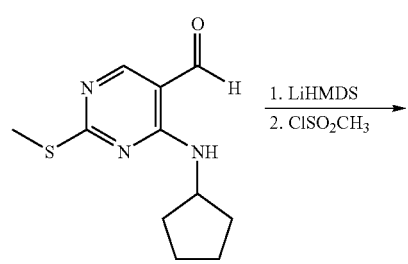
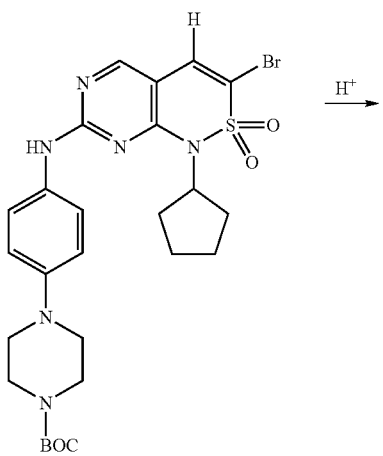
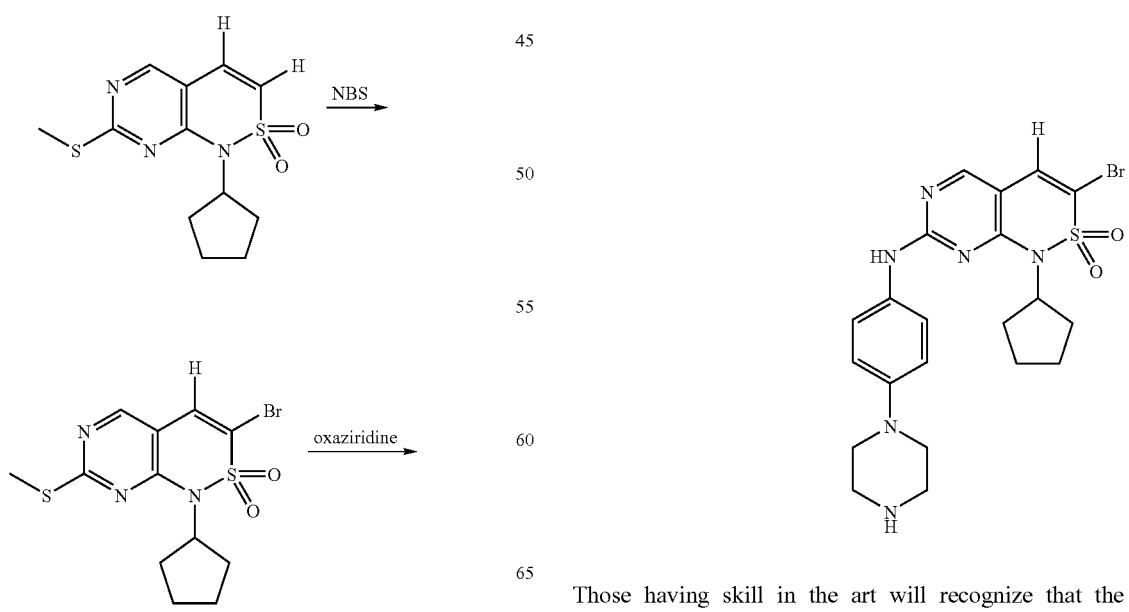
Those having skill in the art will recognize that the starting materials may be varied and additional steps employed to produce compounds encompassed by the present invention, as demonstrated by the following examples.

As shown in Schemes 1 and 2, a 4-substituted amino-2-methansulfanyl-pyrimidine-5-carboxaldehyde or 5-ketone is reacted with an appropriate base, such as, for example, lithium bis(trimethylsilyl) amide followed by addition of an appropriate sulfonyl chloride, to afford the corresponding 2-thia-1,6,8-triaza-naphthalene-2,2-dioxide. In Scheme 1, this 7-methylsulfanyl derivative is subsequently oxidized to the corresponding 7-methylsulfinyl derivative. The 7-methylsulfinyl derivative is subsequently treated with a desired amine to afford the 7-amino compound of the present invention. Additionally this amine may contain protecting groups when necessary to obtain selective regiochemistry, and subsequently deprotected to afford a different 7-phenylamino compound of the present invention.

As shown in Scheme 2, the 7-phenyl-amino (BOC) derivative is hydrogenated with an appropriate catalyst and hydrogen gas to give the (3,4-dihydro)-7-phenyl-amino (BOC) derivative. The subsequent step follows in a similar manner to that of Scheme 1 to a different 7-phenylamino compound of the present invention.

As shown in Scheme 3, the 7-methylsulfanyl derivative is halogenated with an appropriate reagent, e.g. N-bromosuccinimide (NBS) to give the 3-bromo-2-thia-1,6,8-triaza-naphthalene-2,2-dioxide. The subsequent steps follow in a similar manner to that of Scheme 1 to afford 7-amino naphthalene dioxides of the present invention.

The disclosures in this application of all articles and references, including patents, are incorporated herein by reference.

The starting materials and various intermediates may be obtained from commercial sources, prepared from commercially available organic compounds, or prepared using well-known synthetic methods.

Representative examples of methods for preparing intermediates of the invention are set forth below.

The invention is illustrated further by the following examples which are not to be construed as limiting the invention in scope or spirit to the specific procedures described in them.

EXAMPLE 1

1-Cyclopentyl-7-methylsulfanyl-1H-2-thia-1,6,8-triaza-naphthalene 2,2-dioxide

A solution of 4-cyclopentylamino-2-methylsulfanyl-pyrimidine-5-carbaldehyde (prepared as described in WO 98/33798 (incorporated herein by reference)) (30 g, 126 mmol) was suspended in dry THF (700 mL) under argon, and the mixture was cooled to −70° C. A solution of lithium bis(trimethylsilyl) amide, 1.0M in hexane (316 mL, 316 mmol) was added dropwise with stirring over 30 minutes. A solution of methanesulfonylchloride (10.5 ml, 136 mmol) in dry THF (25 mL) was added over 5 minutes, and then the reaction mixture was left to stir at −55° C. for at least 1 hour. An additional portion of methanesulfonylchloride (9 ml, 78 mmol) was added over 2 hours as the temperature was allowed to reach 0° C. The reaction was then cooled to −70° C. and left undisturbed overnight. The reaction mixture was then evaporated in vacuo to an oil and poured into a mixture of diethyl ether (1 L) and 1$\underline{N}$ citric acid solution (375 ml). The pH of the mixture was adjusted to 8 by addition of 4N NaOH, agitated, and the ether phase was decanted. The aqueous phase was extracted with diethylether, the organic phases were combined, washed with water, brine, and dried over anhydrous magnesium sulfate. After removal of the drying agent and evaporation of the solvent, the crude product was purified by chromatography on 300 g silica gel (10%–20% ethyl acetate in hexanes) to yield 7.01 g (18.7% yield) 1-Cyclopentyl-7-methylsulfanyl-1H-2-thia-1,6,8-triaza-naphthalene 2,2-dioxide as a colorless solid. MS: APCI: M+1: 298.1 (M: 297.4).

EXAMPLE 2

1-Cyclopentyl-7-methanesulfinyl-1H-thia-1,6,8-triaza-naphthalene 2,2-dioxide

1-Cyclopentyl-7-methylsulfanyl-2-thia-1,6,8-triaza-naphthalene 2,2-dioxide (6.0 g, 20 mmol) prepared as in Example 1 and 2-benzenesulfonyl- 3-phenyl-oxaziridine (6.3 g, 24 mmol) were dissolved in 50% dichloromethane in methanol (75 ml) and stirred overnight at room temperature. Following evaporation of the solvent, the crude product was purified by recrystallization in diethyl ether/methanol to yield 5.22 g (83% yield) 1-Cyclopentyl-7-methylsulfinyl-1H-thia-1,6,8-triaza-naphthalene 2,2-dioxide as a white solid MS: APCI: M+1: 314.1 (M: 314.3).

EXAMPLE 3

4-[4-(1-Cyclopentyl-2,2-dioxo-1,2-dihydro-2l$^6$-thia-1,6,8-triaza-naphthalen-7-ylamino)-phenyl]-piperazine-1-carboxylic acid tert-butyl ester 1-Cyclopentyl-7-methanesulfinyl-1H-thia-1,6,8-triaza-naphthalene 2,2-dioxide (2.5 g, 7.98 mmol) prepared as in Example 2 and 4-(4-amino-phenyl)-piperazine-1-carboxylic acid tert butyl ester (2.65 g, 9.57 mmol) were dissolved in anhydrous dimethylsulfoxide (6 mL) and heated to 95° C. After 16 hours, the reaction mixture was allowed to cool giving a crystalline solid. The mixture was filtered, diluted with water, and the filtrate was extracted with ethyl acetate and dried over anhydrous magnesium sulfate. The suspension was filtered and evaporated to a paste. The paste was combined with the solid previously obtained from the filtration of the reaction mixture and both were combined and purified by silica gel chromatography on a Biotage® 40M column eluted with chloroform to yield 2.2 g (52% yield) 4-[4-(1-Cyclopentyl-2,2-dioxo-1,2-dihydro-2l$^6$-thia-1,6,8-triaza-naphthalen-7-ylamino)-phenyl]-piperazine-1-carboxylic acid tert-butyl ester as a yellow solid. MS: APCI: M+1: 527.2 (M: 526.7).

EXAMPLE 4

(1-Cyclopentyl-2,2-dioxo-1,2-dihydro-2l$^6$-thia-1,6,8-triaza-naphthalen-7-yl)-(4-piperazin-1-yl-phenyl)-amine 4-[4-(1-Cyclopentyl-2,2-dioxo-1,2-dihydro-2l$^6$-thia-1,6, 8-triaza-naphthalen-7-ylamino)-phenyl]-piperazine-1-carboxylic acid tert-butyl ester (1.3 g, 2.47 mmol) prepared as described in Example 3 was dissolved in a 20:80 mixture of methanol and dichloromethane to which was added a solution of 2N HCl in diethyl ether (10 mL). The suspension was stirred at room temperature for 18 hours, evaporated to a solid and resuspended in a 20:80 mixture of methanol and dichloromethane to which was added anhydrous HCl gas until the mixture reached reflux. The mixture was filtered and the solid was washed with diethyl ether and dried in vacuo yielding 1.32 g (100% yield) (1-Cyclopentyl-2,2-dioxo-1,2-dihydro-2l$^6$-thia-1,6,8-triaza-naphthalen-7-yl)-(4-piperazin-1-yl-phenyl)-amine as a yellow solid. $C_{21}H_{26}N_6O_2S.3HCl.1.75\ H_2O$:

Calcd C, 44.45; H, 5.77; N, 14.81; Cl$^-$, 18.74; H$_2$O, 5.55:. Found: C, 44.52; H, 5.97; N, 14.45; Cl$^-$, 17.94; H$_2$O, 5.42. MS: APCI: M+1: 427.1 (M: 426.2).

EXAMPLE 5

4-[4-(1-Cyclopentyl-2,2-dioxo-1,2-dihydro-2l$^6$-thia-1,6,8-triaza-naphthalen-7-ylamino)-phenyl]2,2-dimethyl-piperazine-1-carboxylic acid tert-butyl ester In a manner similar to that in Example 3, 1-Cyclopentyl-7-methanesulfinyl-1H-thia-1,6,8-triaza-naphthalene 2,2-dioxide (1.20 g, 3.83 mmol) and 4-(4-amino-phenyl)-2,2-dimethyl-piperazine-1-carboxylic acid tert-butyl ester (prepared as in WO 01/70741, (incorporated herein by reference)) (1.40 g, 4.59 mmol) were reacted to yield 1.24 g (58% yield) 4-[4-(1-Cyclopentyl-2,2-dioxo-1,2-dihydro-2l$^6$-thia-1,6,8-triaza-naphthalen-7-ylamino)-phenyl]2,2-dimethyl-piperazine-1-carboxylic acid tert-butyl ester. MS: APCI: M+1: 555.2 (M: 554.7).

EXAMPLE 6

(1-Cyclopentyl-2,2-dioxo-1,2-dihydro-2l$^6$-thia-1,6,8-triaza-naphthalen-7-yl)-[4-(3,3-dimethyl-piperazin-1-yl)-phenyl]-amine In a manner similar to that shown in Example 4, (1.15 g, 2.07 mmol) 4-[4-(1-Cyclopentyl-2,2-dioxo-1,2-dihydro-2l$^6$-thia-1,6,8-triaza-naphthalen-7-ylamino)-phenyl]2,2-dimethyl-piperazine-1-carboxylic acid tert-butyl ester yielded 0.92 g (98% yield) (1-Cyclopentyl-2,2-dioxo-1,2-dihydro-2l$^6$-thia-1,6,8-triaza-naphthalen-7-yl)-[4-(3,3-dimethyl-piperazin-1-yl)-phenyl]-amine as a yellow solid, $C_{23}H_{30}N_6O_2S.2HCl.1H_2O$:

Calcd C, 50.64; H, 6.28; N, 15.41; Cl$^-$, 12.99; H$_2$O, 3.30:. Found: C, 51.00; H, 6.29; N, 15.28; Cl$^-$, 12.78; H$_2$O, 3.18. MS: APCI: M+1: 455.2 (M: 454.2).

EXAMPLE 7

1-Cyclopentyl-3-methyl-7-methylsulfanyl-1H-2-thia-1,6,8-triaza-naphthalene 2,2-dioxide In a manner similar to that shown in Example 1, 1-Cyclopentylamino-2-methanesulfanyl-pyrimidine-5-carboxaldehyde (1.1 g, 4.64 mmol) and ethanesulfonylchloride (3.03 ml, 32 mmol) yielded 0.89 g (8.5% yield) 1-Cyclopentyl-3-methyl-7-methylsulfanyl-1H-2-thia-1,6,8-triaza-naphthalene 2,2-dioxide. MS: APCI: M+1: 312.1 (M: 311.4).

EXAMPLE 8

1-Cyclopentyl-7-methylsulfinyl-3-methyl-1H-2-thia-1,6,8-triaza-naphthalene 2,2-dioxide In a manner similar to that of Example 2, 1-Cyclopentyl-3-methyl-7-methylsulfanyl-1H-2-thia-1,6,8-triaza-naphthalene 2,2-dioxide (0.84 g, 2.71 mmol) and 2-benzenesulfonyl-3-phenyl-oxaziridine (0.846 g, 3.25 mmol) yielded 0.624 g (70% yield) 1-Cyclopentyl-7-methylsulfinyl-3-methyl-1H-2-thia-1,6,8-triaza-naphthalene 2,2-dioxide as a white solid. MS: APCI: M+1: 328.1 (M: 327.4).

EXAMPLE 9

4-[4-(1-Cyclopentyl-3-methyl-2,2-dioxo-1,2-dihydro-2l$^6$-thia-1,6,8-triaza-naphthalen-7-ylamino)-phenyl]-piperazine-1-carboxylic acid tert-butyl ester In a manner similar to that of Example 3, 1-Cyclopentyl-7-methanesulfinyl-3-methyl-1H-2-thia-1,6,8-triaza-naphthalene 2,2-dioxide (0.61 g, 1.86 mmol) and 4-(4aminophenyl)-piperazine-1-carboxylic acid tert butyl ester (0.67 g, 2.41 mmol) yielded 0.62 g (62% yield) 4-[4-(1-Cyclopentyl-3-methyl-2,2-dioxo-1,2-dihydro-2l$^6$-thia-1,6,8-triaza-naphthalen-7-ylamino)-phenyl]-piperazine-1-carboxylic acid tert-butyl ester as a pale yellow solid. MS: APCI: M+1: 541.2 (M: 540.7).

EXAMPLE 10

(1-Cyclopentyl-3-methyl-2,2-dioxo-1,2-dihydro-2l$^6$-thia-1,6,8-triaza-naphthalen-7-yl)-(4-piperazin-1-yl-phenyl)-amine In a manner similar to that shown in Example 4, 4-[4-(1-Cyclopentyl-3-methyl-2,2-dioxo-1,2-dihydro-2l$^6$-thia-1,6,8-triaza-naphthalen-7-ylamino)-phenyl]-piperazine-1-carboxylic acid tert-butyl ester (0.62 g, 1.18 mmol) yielded 0.58 g (100% yield) (1-Cyclopentyl-3-methyl-2,2-dioxo-1,2-dihydro-2l$^6$-thia-1,6,8-triaza-naphthalen-7-yl)-(4-piperazin-1-yl-phenyl)-amine as a white solid.

$C_{22}H_{28}N_6O_2S.2.75HCl.2.25\ H_2O$: Calcd C, 44.45; H, 6.11; N, 14.46; Cl$^-$, 16.77; H$_2$O, 6.97:. Found: C, 45.25; H, 6.09; N, 14.23; Cl$^-$, 16.92; H$_2$O, 6.77. MS: APCI: M+1: 441.2 (M: 440.6).

EXAMPLE 11

1-Cyclopentyl-3-ethyl-7-methylsulfanyl-1H-2-thia-1,6,8-triaza-naphthalene 2,2-dioxide In a manner similar to that shown in Example 1, 1-Cyclopentylamino-2-methanesulfanyl-pyrimidine-5-carboxaldehyde (6.0 g, 25.2 mmol) and propanesulfonylchloride (3.62 ml, 28.9 mmol) yielded 0.62 g (7.6% yield) 1-Cyclopentyl-3-ethyl-7-methylsulfanyl-1H-2-thia-1,6,8-triaza-naphthalene 2,2-dioxide. MS: APCI: M+1: 326.1 (M: 325.5).

EXAMPLE 12

1-Cyclopentyl-3-ethyl-7-methanesulfinyl-1H-2-thia-1,6,8-triaza-naphthalene 2,2-dioxide In a manner similar to that of Example 2, 1-cyclopentyl-3-ethyl-7-methylsulfanyl-1H-2-thia-1,6,8-triaza-naphthalene 2,2-dioxide (0.86 g, 2.64 mmol) and 2-benzenesulfonyl-3-phenyl-oxaziridine (0.83 g, 3.17 mmol) yielded 0.67 g (74% yield) 1-Cyclopentyl-3-ethyl-7-methanesulfinyl-1H-2-thia-1,6,8-triaza-naphthalene 2,2-dioxide as a white solid. MS: APCI: M+1: 342.1 (M: 341.5).

EXAMPLE 13

4-[4-(1-Cyclopentyl-3-ethyl-2,2-dioxo-1,2-dihydro-2$l^6$-thia-1,6,8-triaza-naphthalen-7-ylamino)-phenyl]-piperazine-1-carboxylic acid tert-butyl ester In a manner similar to that of Example 3, 1-Cyclopentyl-3-ethyl-7-methanesulfinyl-1H-2-thia-1,6,8-triaza-naphthalene 2,2-dioxide (0.66 g, 1.92 mmol) and 4-(4amino-phenyl)-piperazine-1-carboxylic acid tert butyl ester (0.72 g, 2.59 mmol) yielded 0.75 g (70% yield) 4-[4-(1-Cyclopentyl-3-ethyl-2,2-dioxo-1,2-dihydro-2$l^6$-thia-1,6,8-triaza-naphthalen-7-ylamino)-phenyl]-piperazine-1-carboxylic acid tert-butyl ester as a pale yellow solid. MS: APCI: M+1: 555.3 (M: 554.7).

EXAMPLE 14

(1-Cyclopentyl-3-ethyl-2,2-dioxo-1,2-dihydro-2$l^6$-thia-1,6,8-triaza-naphthalen-7-yl)-(4-piperazin-1-yl-phenyl)-amine In a manner similar to that shown in Example 4,4-[4-(1-Cyclopentyl-3-ethyl-2,2-dioxo-1,2-dihydro-2$l^6$-thia-1,6,8-triaza-naphthalen-7-ylamino)-phenyl]-piperazine-1-carboxylic acid tert-butyl ester (0.72 g, 1.3 mmol) yielded 0.66 g (100% yield) (1-Cyclopentyl-3-ethyl-2,2-dioxo-1,2-dihydro-2$l^6$-thia-1,6,8-triaza-naphthalen-7-yl)-(4-piperazin-1-yl-phenyl)-amine as a pale yellow solid.

$C_{23}H_{30}N_6O_2S.2HCl.0.5 H_2O$: Calcd C, 51.49; H, 6.20; N, 15.66; Cl$^-$, 13.21; H$_2$O, 1.67:. Found: C, 51.49; H, 6.20; N, 15.66; Cl$^-$, 13.28; H$_2$O, 1.53. MS: APCI: M+1: 455.2 (M: 454.6).

EXAMPLE 15

4-[4-(1-Cyclopentyl-2,2-dioxo-1,2,3,4-tetrahydro-2$l^6$-thia-1,6,8-triaza-naphthalen-7-ylamino)-phenyl]-piperazine-1-carboxylic acid tert-butyl ester 4-[4-(1-Cyclopentyl-2,2-dioxo-1,2-dihydro-2$l^6$-thia-1,6,8-triaza-naphthalen-7-ylamino)-phenyl]-piperazine-1-carboxylic acid tert-butyl ester (0.56 g, 1.06 mmol) and Raney nickel catalyst were placed in a reactor with tetrahydrofuran (40 ml) and methanol (10 ml). The reactor was pressurized with H$_2$ gas and heated at 40° C. for 48 hours. The resulting suspension was filtered, evaporated to a solid and recrystallized from diethyl ether and chloroform which yielded 0.45 g (81% yield) 4-[4-(1-Cyclopentyl-2,2-dioxo-1,2,3,4-tetrahydro-2$l^6$-thia-1,6,8-triaza-naphthalen-7-ylamino)-phenyl]-piperazine-1-carboxylic acid tert-butyl ester as a white solid. MS: APCI: M+1: 529.1 (M: 528.8)

EXAMPLE 16

(1-Cyclopentyl-2,2-dioxo-1,2,3,4-tetrahydro-2$l^6$-thia-1,6,8-triaza-naphthalen-7-yl)-(4-piperazin-1-yl-phenyl)-amine When treated in a manner similar to that of Example 4, 4-[4-(1-Cyclopentyl-2,2-dioxo-1,2,3,4-tetrahydro-2$l^6$-thia-1,6,8-triaza-naphthalen-7-ylamino)-phenyl]-piperazine-1-carboxylic acid tert-butyl ester (0.45 g, 0.85 mmol) yielded 0.48 g (100% yield) (1-Cyclopentyl-2,2-dioxo-1,2,3,4-tetrahydro-2$l^6$-thia-1,6,8-triaza-naphthalen-7-yl)-(4-piperazin-1-yl-phenyl)-amine as a white solid. $C_{21}H_{28}N_6O_2S.3HCl.1.75 H_2O$: Calcd C, 44.29; H, 6.11; N, 14.71; Cl$^-$, 18.67; H$_2$O, 5.53:. Found: C, 44.37; H, 6.16; N, 14.67; Cl$^-$, 18.06; H$_2$O, 5.76. MS: APCI: M+1: 429.2 (M: 428.2).

EXAMPLE 17

1-Ethyl-3-methyl-7-methylsulfanyl-1H-2-thia-1,6,8-triaza-naphthalene 2,2-dioxide In a manner similar to that shown in Example 1, 1-Ethylamino-2-methylsulfanyl-pyrimidine-5-carbaldehyde (7.2 g, 36.5 mmol) and ethanesulfonylchloride (3.49 ml, 39.4 mmol) yielded 0.49 g (4.9% yield) 1-Ethyl-7-methylsulfanyl-3-methyl-1H-2-thia-1,6,8-triaza-naphthalene 2,2-dioxide. MS: APCI: M+1: 271.9 (M: 271.0).

EXAMPLE 18

1-Ethyl-7-methylsulfinyl-3-methyl-1H-2-thia-1,6,8-triaza-naphthalene 2,2-dioxide In a manner similar to that of Example 2, 1-Ethyl-3-methyl-7-methylsulfanyl-1H-2-thia-1,6,8-triaza-naphthalene 2,2-dioxide (0.47 g, 1.73 mmol) and 2-benzenesulfonyl-3-phenyl-oxaziridine (0.54 g, 2.1 mmol) yielded 0.28 g (57% yield) 1-Ethyl-7-methylsulfinyl-3-methyl-1H-2-thia-1,6,8triaza-naphthalene 2,2-dioxide as a white solid MS: APCI: M+1: 288.0 (M: 287.0).

EXAMPLE 19

4-[4-(1-Ethyl-3-methyl-2,2-dioxo-1,2-dihydro-2$l^6$-thia-1,6,8-triaza-naphthalen-7-ylamino)-phenyl]-piperazine-1-carboxylic acid tert-butyl ester In a manner similar to that of Example 3, 1-Ethyl-7-methanesulfinyl-3-methyl-1H-2-thia-1,6,8-triaza-naphthalene 2,2-dioxide (0.27 g, 0.94 mmol) and 4-(4-amino-phenyl)-piperazine-1-carboxylic acid tert butyl ester (0.31 g, 1.13 mmol) yielded 0.21 g (45% yield) 4-[4-(1-Ethyl-3-methyl-2,2-dioxo-1,2-dihydro-2$l^6$-thia-1,6,8-triaza-naphthalen-7-ylamino)-phenyl]-piperazine-1-carboxylic acid tert-butyl ester as a yellow solid. MS: APCI: M+1: 501.1 (M: 500.6).

EXAMPLE 20

(1-Ethyl-3-methyl-2,2-dioxo-1,2-dihydro-2$l^6$-thia-1,6,8-triaza-naphthalen-7-yl)-(4-piperazin-1-yl-phenyl)-amine In a manner similar to that shown in Example 4, 4-[4-(1-Ethyl-3-methyl-2,2-dioxo-1,2-dihydro-2$l^6$-thia-1,6,8-triaza-naphthalen-7-ylamino)-phenyl]-piperazine-1-carboxylic acid tert-butyl ester (0.20 g, 0.41 mmol) yielded 0.18 g (100% yield) (1-Ethyl-3-methyl-2,2-dioxo-1,2-dihydro-2$l^6$-thia-1,6,8-triaza-naphthalen-7-yl)-(4-piperazin-1-yl-phenyl)-amine as a white solid.

$C_{19}H_{24}N_6O_2S.3HCl.0.5 H_2O$: Calcd C, 43.98; H, 5.44; N, 16.19; Cl$^-$, 20.50; H$_2$O, 1.74:. Found: C, 44.05; H, 5.35; N, 16.13; Cl$^-$, 20.03; H$_2$O, 1.99.

The following compounds are prepared according to the procedures described in Examples 1 to 20 and shown in Schemes 1, 2 and 3:

1-Cyclopentyl-7-methylsulfanyl-1H-2-thia-1,6,8-triaza-naphthalene 2,2-dioxide (Compound 1), 1-Cyclopentyl-7-methanesulfinyl-1H-thia-1,6,8-triaza-naphthalene 2,2-dioxide (Compound 2), 4-[4-(1-Cyclopentyl-2,2-dioxo-1,2-dihydro-2$l^6$-thia-1,6,8-triaza-naphthalen-7-ylamino)-phenyl]-piperazine-1-carboxylic acid tert-butyl ester (Compound 3), (1-Cyclopentyl-2,2-dioxo-1,2-dihydro-2$l^6$-thia-1,6,8-triaza-naphthalen-7-yl)-(4-piperazin-1-yl-phenyl)-amine (Compound 4), 4-[4-(1-Cyclopentyl-2,2-dioxo-1,2-dihydro-2$l^6$-thia-1,6,8-triaza-naphthalen-7-ylamino)-phenyl]2,2-dimethyl-piperazine-1-carboxylic acid tert-butyl ester (Compound 5), (1-Cyclopentyl-2,2-dioxo-1,2-dihydro-2$l^6$-thia-1,6,8-triaza-naphthalen-7-yl)-[4-(3,3-dimethyl-piperazin-1-yl)-phenyl]-amine (Compound 6), 1-Cyclopentyl-3-methyl-7-methylsulfanyl-1H-2-thia-1,6,8-triaza-naphthalene 2,2-dioxide (Compound 7), 1-Cyclopentyl-7-methylsulfinyl-3-methyl-1H-2-thia-1,6,8-triaza-naphthalene 2,2-dioxide (Compound 8), 4-[4-(1-Cyclopentyl-3-methyl-2,2-dioxo-1,2-dihydro-2$l^6$-thia-1,6,8-triaza-naphthalen-7-ylamino)-phenyl]-piperazine-1-carboxylic acid tert-butyl ester (Compound 9), (1-Cyclopentyl-3-methyl-2,2-dioxo-1,2-dihydro-2$l^6$-thia-1,6,8-triaza-naphthalen-7-yl)-(4-piperazin-1-yl-phenyl)-amine (Compound 10), 1-Cyclopentyl-3-ethyl-7-methylsulfanyl-1H-2-thia-1,6,8-triaza-naphthalene 2,2-dioxide (Compound 11), 1-Cyclopentyl-3-ethyl-7-methanesulfinyl-1H-2-thia-1,6,8-triaza-naphthalene 2,2-dioxide (Compound 12), 4-[4-(1-Cyclopentyl-3-ethyl-2,2-dioxo-1,2-dihydro-2$l^6$-thia-1,6,8-triaza-naphthalen-7-ylamino)-phenyl]-piperazine-1-carboxylic acid tert-butyl ester (Compound 13), (1-Cyclopentyl-3-ethyl-2,2-dioxo-1,2-dihydro-2$l^6$-thia-1,6,8-triaza-naphthalen-7-yl)-(4-piperazin-1-yl-phenyl)-amine (Compound 14), 4-[4-(1-Cyclopentyl-2,2-dioxo-1,2,3,4-tetrahydro-2$l^6$-thia-1,6,8-triaza-naphthalen-7-ylamino)-phenyl]-piperazine-1-carboxylic acid tert-butyl ester (Compound 15), (1-Cyclopentyl-2,2-dioxo-1,2,3,4-tetrahydro-2$l^6$-thia-1,6,8-triaza-naphthalen-7-yl)-(4-piperazin-1-yl-phenyl)-amine (Compound 16)

1-Ethyl-3-methyl-7-methylsulfanyl-1H-2-thia-1,6,8-triaza-naphthalene 2,2-dioxide (Compound 17), 1-Ethyl-7-methylsulfinyl-3-methyl-1H-2-thia-1,6,8-triaza-naphthalene 2,2-dioxide (Compound 18), 4-[4-(1-Ethyl-3-methyl-2,2-dioxo-1,2-dihydro-2$l^6$-thia-1,6,8-triaza-naphthalen-7-ylamino)-phenyl]-piperazine-1-carboxylic acid tert-butyl ester (Compound 19), (1-Ethyl-3-methyl-2,2-dioxo-1,2-dihydro-2$l^6$-thia-1,6,8-triaza-naphthalen-7-yl)-(4-piperazin-1-yl-phenyl)-amine (Compound 20), (1-Cyclopentyl-2,2-dioxo-1,2-dihydro-2$l^6$-thia-1,6,8-triaza-naphthalen-7-yl)-[4-(3,5-dimethyl-piperazin-1-yl)-phenyl]-amine (Compound 21), (1-Isopropyl-2,2-dioxo-1,2-dihydro-2$l^6$-thia-1,6,8-triaza-naphthalen-7-yl)-(4-piperazin-1-yl-phenyl)-amine (Compound 22), (1-Cyclopentyl-4-methyl-2,2-dioxo-1,2-dihydro-2$l^6$-thia-1,6,8-triaza-naphthalen-7-yl)-(4-piperazin-1-yl-phenyl)-amine (Compound 23), (3-Bromo-1-cyclopentyl-2,2-dioxo-1,2-dihydro-2$l^6$-thia-1,6,8-triaza-naphthalen-7-yl)-(4-piperazin-1-yl-phenyl)-amine (Compound 24),

[4-(3-Amino-cyclopentyl)phenyl](1-cyclopentyl-2,2-dioxo-1,2-dihydro-2$l^6$-thia-1,6,8-triaza-naphthalen-7-yl)-amine (Compound 25), (3-Chloro-4-piperazin-1-yl)-(1-cyclopentyl-2,2-dioxo-1,2-dihydro-2$l^6$-thia-1,6,8-triaza-naphthalen-7-yl)-amine (Compound 26), (1-Cyclopentyl-2,2-dioxo-1,2-dihydro-2$l^6$-thia-1,6,8-triaza-naphthalen-7-yl)-(4-morpholin-4-yl-phenyl)-amine (Compound 27), (1-Cyclopentyl-2,2-dioxo-1,2-dihydro-2$l^6$-thia-1,6,8-triaza-naphthalen-7-yl)-(5-piperazin-1-yl-pyridin-2-yl)-amine (Compound 28), (1-Cyclohexyl-2,2-dioxo-1,2-dihydro-2$l^6$-thia-1,6,8-triaza-naphthalen-7-yl)-[4-(3,3-dimethyl-piperazin-1-yl)-phenyl]-amine (Compound 29), (3-Bromo-1-cyclopentyl-2,2-dioxo-1,2-dihydro-2$l^6$-thia-1,6,8-triaza-naphthalen-7-yl)-[4-(3,5-dimethyl-piperazin-1-yl-phenyl)-amine (Compound 30), (1-Isopropyl-3-methyl-2,2-dioxo-1,2-dihydro-2$l^6$-thia-1,6,8-triaza-naphthalen-7-yl)-(4-piperazin-1-yl-phenyl)-amine (Compound 31), (1-Cyclopentyl-2,2-dioxo-1,2-dihydro-2$l^6$-thia-1,6,8-triaza-naphthalen-7-yl)-[4-(3,3-dimethyl-piperazin-1-yl)-phenyl]-amine (Compound 32), (1-Cyclopentyl-2,2-dioxo-1,2,3,4-tetrahydro-2$l^6$-thia-1,6,8-triaza-naphthalen-7-yl)-(4-piperazin-1-yl-phenyl)-amine (Compound 33),

[1-Cyclopentyl-2,2-dioxo-7-(4-piperazin-1-yl-phenylamino 1,2-dihydro-2$l^6$-thia-1,6,8-triaza-naphthalen-3-yl]-methanol (Compound 34), (1-Cyclohexyl-2,2-dioxo-1,2,3,4-tetrahydro-2$l^6$-thia-1,6,8-triaza-naphthalen-7-yl)-[4-(3,3-dimethyl-piperazin-1-yl)-phenyl]-amine (Compound 35), (1-Cyclopentyl-2,2-dioxo-1,2,3,4-tetrahydro-2$l^6$-thia-1,6,8-triaza-naphthalen-7-yl)-[4-(3,5-dimethyl-piperazin-1-yl)-phenyl]-amine (Compound 36), (1-Isopropyl-3-methyl-2,2-dioxo-1,2,3,4-tetrahydro-2$l^6$-thia-1,6,8-triaza-naphthalen-7-yl)-(4-piperazin-1-yl-phenyl)-amine (Compound 37).

EXAMPLE 21

Biological Assays

In order to determine the selectivity of the compounds of the present inventions, representative compounds were evaluated in standard assays routinely used to measure inhibition of cyclin-dependent kinase enzymes and other serine/threonine protein kinases. The assays were carried out as follows:

Assay for Inhibition of cdk1 and cdk2

Cdk1 and cdk2 enzyme assays for $IC_{50}$ determinations and kinetic evaluation were performed as follows. 96-well filter plates (Millipore MADVN6550) were used. The total volume of each well in the assay was 0.1 mL in Buffer A (20 mM TRIS (pH 7.4), 50 mM NaCl, 1 mM dithiothreitol, 10 mM $MgCl_2$), to which was added 12 mM ATP containing 0.25 μCi [$^{32}$P]ATP, 20 ng enzyme (cdk2/cyclin E, cdk2/cyclin A, or cdk1/cyclin B), 1 μg retinoblastoma protein, and appropriate dilutions in Buffer A of the particular test compound. Buffer A alone without added test compound was employed as a control for no inhibition. Buffer A containing excess EDTA was used to determine the level of background $^{32}$P in the absence of enzyme activity. All components except the ATP were added to the wells, and the plate was placed on a plate mixer for 2 minutes. The reaction was initiated by addition of [$^{32}$P]ATP, and the plate was incubated at 25° C. for 15 minutes. The reaction was terminated by addition of 0.1 mL 20% TCA. The plate was kept at 4° C. for at least 1 hour to allow the substrate to precipitate. The wells were then washed five times with 0.2 mL 10% TCA, and $^{32}P$ incorporation was determined with a beta plate counter (Wallac Inc., Gaithersburg, Md.). The $IC_{50}$ of the test compound was determined using the median effect method (Chou, T-C and Talalay, P. Applications of the median effect principle for the assessment of low-dose risk of carcinogens and for the quantitation of synergism and antagonism of chemotherapeutic agents. In: New Avenues in Developmental Cancer Chemotherapy (Eds. Harrap, K. T. and Connors, T. A.), pp. 37–64. Academic Press, New York, 1987).

Assay for Inhibition of cdk4/Cyclin D

The cdk4 enzyme assay for $IC_{50}$ determination and kinetic evaluation was performed as follows: 96-well filter plates (Millipore MADVN6550) were used. The total volume was 0.1 mL containing a final concentration of buffer A (20 mM TRIS (tris[hydroxymethyl]aminomethane) (pH 7.4), 50 mM NaCl, 1 mM dithiothreitol, 10 mM $MgCl_2$), 25 μM ATP containing 0.25 μCi [$^{32}P$]ATP, 20 ng Cdk4, 1 μg retinoblastoma protein, and the test compound at appropriate dilutions in buffer A. Buffer A alone without added test compound was employed as a control for no inhibition. Buffer A containing excess EDTA was used to determine the level of background $^{32}P$ in the absence of enzyme activity. All components except the ATP were added to the wells, and the plate was placed on a plate mixer for 2 minutes. The reaction was started by adding [$^{32}P$]ATP, and the plate was incubated at 25° C. for 15 minutes. The reaction was terminated by addition of 0.1 mL 20% trichloroacetic acid (TCA). The plate was kept at 4° C. for at least 1 hour to allow the substrate to precipitate. The wells were then washed five times with 0.2 mL 10% TCA, and $^{32}P$ incorporation was determined with a beta plate counter (Wallac Inc., Gaithersburg, Md.).

For PDGF receptor (PDGFr) and FGF receptor (FGFr) tyrosine kinase assays, full-length cDNAs for the mouse PDGF-β and human FGF1(flg) receptor tyrosine kinases were obtained from J. Escobedo and prepared as described previously (Escobedo et al., *J. Biol. Chem.*, 1988;262: 1482–1487). PCR primers were designed to amplify a fragment of DNA that codes for the intracellular tyrosine kinase domain. The fragment was inserted into a baculovirus vector, cotransfected with AcMNPV DNA, and the recombinant virus was isolated. SF9 insect cells are infected with the virus to overexpress the protein, and the cell lysate was used for the assay.

PDGFr and FGFr enzyme assays were performed in 96-well plates (100 μL/incubation/well), and conditions were optimized to measure the incorporation of $^{32}P$ from [$\gamma^{32}P$]ATP into a glutamate-tyrosine co-polymer substrate. Briefly, to each well was added 82.5 μL incubation buffer containing 25 mM Hepes (pH 7.0), 150 mM NaCl, 0.1% Triton X-100, 0.2 mM PMSF, 0.2 mM $Na_3VO_4$, 10 mM $MnCl_2$, and 750 μg/mL Poly (4:1) glutamate-tyrosine followed by 2.5 μL inhibitor and 5 μL enzyme lysate (7.5 μg/μL FGFr or 6.0 μg/μL PDGFr) to initiate the reaction. Following a 10-minute incubation at 25° C., 10 mL [$\gamma^{32}P$]ATP (0.4 μCi plus 50 μM ATP) was added to each well, and samples were incubated for an additional 10 minutes at 25° C. The reaction was terminated by the addition of 100 μL 30% trichloroacetic acid (TCA) containing 20 mM sodium pyrophosphate and precipitation of material onto glass fiber mats (Wallac). Filters were washed three times with 15% TCA containing 100 mM sodium pyrophosphate, and the radioactivity retained on the filters was counted in a Wallac 1250 Betaplate reader. Nonspecific activity was defined as radioactivity retained on the filters following incubation of samples with buffer alone (no enzyme). Specific enzymatic activity (enzyme plus buffer) was defined as total activity minus nonspecific activity. The concentration of a compound that inhibited specific activity by 50% ($IC_{50}$) was determined based on the inhibition curve.

The results of the foregoing assays for several compounds of the present invention are presented in Table 2.

TABLE 2

| Compound Number | CYCK1B $IC_{50}$ μM | CYCK2A $IC_{50}$ μM | CYCK2E $IC_{50}$ μM | CYCK4 $IC_{50}$ μM | FGF $IC_{50}$ μM | PDGF $IC_{50}$ μM |
|---|---|---|---|---|---|---|
| 4 | 0.360 | 0.106 | 0.145 | 0.005 | 0.179 | 1.070 |
| 6 | 3.605 | 0.294 | 0.6 | 0.0013 | NA | NA |
| 10 | 36. | 5.454 | 26 | 0.093 | 0.575 | 0.290 |
| 14 | 0 | 4 | >5 | 0.050 | 1.030 | 0.216 |
| 16 | 4.14 | 0.930 | 0.930 | 0.045 | NA | NA |

NA = Data not available.

From the results displayed in Table 2, it is clear that representative Compound 4, (1-Cyclopentyl-2,2-dioxo-1,2-dihydro-2l$^6$-thia-1,6,8-triaza-naphthalen-7-yl)-(4-piperazin-1-yl-phenyl)-amine specifically inhibits Cdk4, and has relatively less effect on cdk1, cdk2, FGF and PDGF.

FORMULATION EXAMPLES

As noted above, the compounds of the present invention will typically be formulated with common excipients, diluents, and carriers to provide compositions that are well-suited for convenient administration to mammals. The following examples illustrate typical compositions that are provided in a further embodiment of this invention.

EXAMPLE 22

| Tablet Formulation | |
|---|---|
| Ingredient | Amount |
| Compound 4 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

Compound 4 was mixed with the lactose and cornstarch (for mix) and blended to uniformity to a powder. The cornstarch (for paste) was suspended in 6 mL of water and heated with stirring to form a paste. The paste was added to the mixed powder, and the mixture was granulated. The wet granules are passed through a No. 8 hard screen and dried at 50° C. The mixture was lubricated with 1% magnesium stearate and compressed into a tablet. The tablets are administered to a patient at the rate of 1 to 4 each day for prevention and treatment of atherosclerosis.

EXAMPLE 23

Parenteral Solution

In a solution of 700 mL of propylene glycol and 200 mL of water for injection was added 20.0 g of Compound 4. The mixture was stirred and the pH was adjusted to 5.5 with hydrochloric acid. The volume was adjusted to 1000 mL with water for injection. The solution was sterilized, filled into 5.0 mL ampoules, each containing 2.0 mL (40 mg of Compound 4), and sealed under nitrogen. The solution was administered by injection to a patient suffering from cancer and in need of treatment.

The invention and the manner and process of making and using it, are now described in such full, clear, concise, and exact terms as to enable any person skilled in the art to which it pertains, to make and use the same. It was to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula I

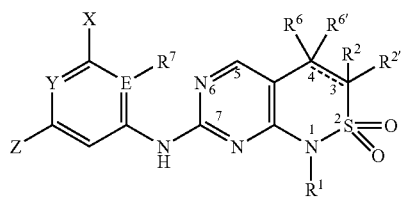

I wherein:

$R^1$ is (a) hydrogen;

(b) lower alkyl optionally substituted with one, two, or three groups independently selected from halogen, hydroxy, lower alkoxy, amino, mono- or dialkylamino, carboxy, alkoxycarbonyl, thioalkyl, nitrile, aryl, heteroaryl containing one or more aromatic ring systems of 5-, or 6-membered rings containing at least one and up to four heteroatoms selected from nitrogen, oxygen, or sulfur, or a carbocyclic cycloalkyl group containing from 3–7 members, up to two of which members are optionally heteroatoms independently selected from oxygen, sulfur, and nitrogen; or (c) a cycloalkyl group containing from 3–7 members, up to two of which members are optionally heteroatoms independently selected from oxygen, sulfur, and nitrogen, wherein the cycloalkyl group is unsubstituted or substituted with one, two or three groups independently selected from halogen, hydroxy, lower alkyl, lower alkoxy, amino, mono- or dialkylamino, aryl, and heteroaryl containing one or more aromatic ring systems of 5-, or 6-membered rings containing at least one and up to four heteroatoms selected from nitrogen, oxygen, or sulfur;

$R^2$ and $R^{2'}$ are independently hydrogen, lower alkyl, lower hydroxy alkyl, lower alkoxy, halogen, haloalkyl, lower alkynyl, lower alkenyl, nitrile, nitro, $C_3$–$C_7$ cycloalkyl, —$OR^3$, —$COR^3$, —$CO_2R^3$, —$CONR^3R^4$, —$SO_2NR^3R^4$, —$SO_2R^3$, —$NCOR^3R^4$, —$NSO_2R^3R^4$, —$NR^3R^4$, —$(CR^3R^4)_mNR^8R^{9'}$, —$(CR^3R^4)_mOR^8$, —$(CR^3R^4)_m$-aryl, —$(CR^3R^4)_m$-heteroaryl, -$T(CH_2)_mQR$, —$C(O)T(CH_2)_mQR^3$, —$NR^3C(O)T(CH_2)_mQR^4$, —$CR^3$=$CR^4C(O)R^8$, or —$SR^4$;

wherein $R^{2'}$ is absent when the bond between C3 and C4 is a carbon-carbon double bond;

E is C or N; and $R^7$ is hydrogen, halogen, lower alkyl, lower alkoxy, or alkylcarbonyl, provided that $R^7$ is absent when E is N;

Y is N or $CR^5$;

$R^6$ and $R^{6'}$ are independently hydrogen, hydroxy, lower alkyl or haloalkyl, wherein $R^{6'}$ is absent when the bond between C3 and C4 is a carbon-carbon double bond, or when $R^6$ is hydroxy, then $R^{6'}$=HU;

X and Z are independently hydrogen, halogen, lower alkyl, lower alkoxy, trifluoromethyl, hydroxy, nitrile, nitro, —$NR^3R^4$, —$N(O)R^3R^4$, —$SR^3$, —$C(O)R^3$, —$CO_2R^3$, —$CONR^3R^4$, —$SO_2NR^3R^4$, —$SO_2R^3$, -$T(CH_2)_mQR^3$, —$C(O)T(CH_2)_mQR^3$, or —$NR^3C(O)T(CH_2)_mQR^4$;

m is 0–6;

T is O, S, $NR^3$, $N(O)R^3$, or $CR^3R^4$;

Q is O, S, $NR^3$, $N(O)R^3$, or $CO_2$;

$R^5$ is $NR^3R^4$, $N(O)R^3R^4$, OH, $OR^3$, $SR^3$, halo, $COR^3$, $(CH_2)_mR^3$, $CO_2R^3$, $CONR^3R^4$, $S(O)_nR^3$, $SO_2R^3$, $SO_2NR^3R^4$, $NR^3SO_2R^4$, nitrile, nitro, alkyl, alkoxyalkyl, $T(CH_2)_mQR^3$, $C(O)T(CH_2)_mQR^3$, $NR^3C(O)T(CH_2)_mQR^4$, or $T(CH_2)_mCO_2R^3$;

Each of $R^3$ and $R^4$ are independently hydrogen, lower alkyl, lower alkenyl, lower alkynyl, $(CH_2)_mAr$, arylalkyl, aryl, heteroarylalkyl, cycloalkyl, heterocyclic containing 5–10-membered rings containing at least one and up to three heteroatoms selected from nitrogen, oxygen, or sulfur, or heteroaryl containing one or more aromatic ring systems of 5-, or 6-membered rings containing at least one and up to four heteroatoms selected from nitrogen, oxygen, or sulfur, or $R^3$ and $R^4$ together with the nitrogen to which they are attached form a cycloalkyl ring containing 3–8 members, up to four of which members are optionally carbonyl groups or heteroatoms independently selected from oxygen, sulfur, S(O), $S(O)_2$, and nitrogen, wherein the cycloalkyl group is unsubstituted or substituted with one, two, three, or four groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, mono- or dialkylamino, N-hydroxyacetamido, aryl, heteroaryl containing one or more aromatic ring systems of 5-, or 6-membered rings containing at least one and up to four heteroatoms selected from nitrogen, oxygen, or sulfur, carboxyalkyl, —$NR^8SO_2R^9$, —$C(O)NR^8R^9$, —$NR^8C(O)R^9$, —$C(O)OR^8$, —$(CH_2)_mS(O)_nR^8$, —$(CH_2)_m$-heteroaryl, —$O(CH_2)_m$-heteroaryl, —$(CH_2)_mC(O)NR^8R^9$, or —$O(CH_2)_mC(O)OR^8$;

n is 0–2;

Each of $R^8$ and $R^9$ are independently hydrogen, lower alkyl, lower alkenyl, lower alkynyl, $(CH_2)_mAr$, arylalkyl, aryl, heteroarylalkyl, cycloalkyl, heterocyclic, or heteroaryl containing one or more aromatic ring systems of 5-, or 6-membered rings containing at least one and up to four heteroatoms selected from nitrogen, oxygen, or sulfur; or a pharmaceutically acceptable salt thereof.

2. A compound of the Formula II

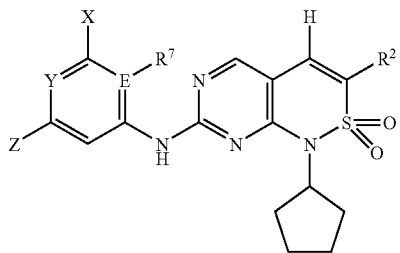

II or a pharmaceutically acceptable salt thereof, wherein:

$R^2$ is hydrogen, lower alkyl, lower hydroxyalkyl, lower alkoxy, halogen, haloalkyl, lower alkynyl, lower alkenyl, nitrile, nitro, $C_3$–$C_7$ cycloalkyl, $-OR^3$, $-COR^3$, $-CO_2R^3$, $-CONR^3R^4$, $-SO_2NR^3R^4$, $-SO_2R^3$, $-NCOR^3R^4$, $-NSO_2R^3R^4$, $-NR^3R^4$, $-(CR^3R^4)_m NR^8R^9$, $-(CR^3R^4)_m OR^8$, $-CR^3R^4)_m$-aryl, $-(CR^3R^4)_m$-heteroaryl, $-T(CH_2)_mQR$, $-C(O)T(CH_2)_m QR^3$, $-NR^3C(O)T(CH_2)_m QR^4$, $-CR^3=CR^4C(O)R^8$, or $-SR^4$;

E is C or N, provided that $R^7$ is absent when E is N; and $R^7$ is hydrogen, halogen, lower alkyl, lower alkoxy, or alkylcarbonyl;

Y is N or $CR^5$;

X and Z are independently hydrogen, halogen, lower alkyl, lower alkoxy, trifluoromethyl, hydroxy, nitrile, nitro, $-NR^3R^4$, $-N(O)R^3R^4$, $-SR^3$, $-C(O)R^3$, $-CO_2R^3$, $-CONR^3R^4$, $-SO_2NR^3R^4$, $-SO_2R^3$, $-T(CH_2)_mQR^3$, $-C(O)T(CH_2)_mQR^3$, or $-NR^3C(O)T(CH_2)_mQR^4$;

m is 0–6;

T is O, S, $NR^3$, $N(O)R^3$, or $CR^3R^4$;

Q is O, S, $NR^3$, $N(O)R^3$, or $CO_2$;

$R^5$ is $NR^3R^4$, $N(O)R^3R^4$, OH, $OR^3$, $SR^3$, halo, $COR^3$, $(CH_2)_mR^3$, $CO_2R^3$, $CONR^3R^4$, $S(O)_nR^3$, $SO_2R^3$, $SO_2NR^3R^4$, $NR^3SO_2R^4$, nitrile, nitro, alkyl, alkoxyalkyl, $T(CH_2)_mQR^3$, $C(O)T(CH_2)_mQR^3$, $NR^3C(O)T(CH_2)_mQR^4$, or $T(CH_2)_mCO_2R^3$;

Each of $R^3$ and $R^4$ are independently hydrogen, lower alkyl, lower alkenyl, lower alkynyl, $(CH_2)_mAr$, arylalkyl, aryl, heteroarylalkyl, cycloalkyl, heterocyclic containing 5–10-membered rings containing at least one and up to three heteroatoms selected from nitrogen, oxygen, or sulfur, or heteroaryl containing one or more aromatic ring systems of 5- or 6-membered rings containing at least one and up to four heteroatoms selected from nitrogen, oxygen, or sulfur, or $R^3$ and $R^4$ together with the nitrogen to which they are attached form a cycloalkyl ring containing 3–8 members, up to four of which members are optionally carbonyl groups or heteroatoms independently selected from oxygen, sulfur, S(O), $S(O)_2$, and nitrogen, wherein the cycloalkyl group is unsubstituted or substituted with one, two, three, or four groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, mono- or dialkylamino, N-hydroxyacetamido, aryl, heteroaryl containing one or more aromatic ring systems of 5- or 6-membered rings containing at least one and up to four heteroatoms selected from nitrogen, oxygen, or sulfur, carboxyalkyl, $-NR^8SO_2R^9$, $-C(O)NR^8R^9$, $-NR^8C(O)R^{49}$, $-C(O)OR^8$, $-(CH_2)_mS(O)_nR^8$, $-(CH_2)_m$-heteroaryl, $O(CH_2)_m$-heteroaryl, $-(CH_2)_mC(O)NR^8R^9$, or $-O(CH_2)_mC(O)OR^8$; and n is 0–2; and Each of $R^8$ and $R^9$ are independently hydrogen, lower alkyl, lower alkenyl, lower alkynyl, $(CH_2)_mAr$, arylalkyl, aryl, heteroarylalkyl, cycloalkyl, heterocyclic containing 5–10-membered rings containing at least one and up to three heteroatoms selected from nitrogen, oxygen, or sulfur, or heteroaryl containing one or more aromatic ring systems of 5- or 6-membered rings containing at least one and up to four heteroatoms selected from nitrogen, oxygen, or sulfur.

3. A compound of the Formula III

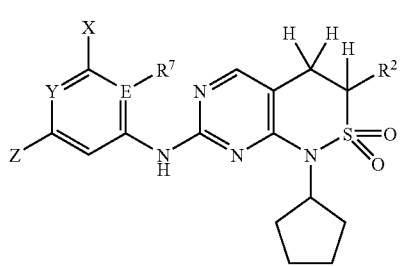

III or a pharmaceutically acceptable salt thereof, wherein:

$R^2$ is hydrogen, lower alkyl, lower hydroxyalkyl, lower alkoxy, halogen, haloalkyl, lower alkynyl, lower alkenyl, nitrile, nitro, $C_3$–$C_7$ cycloalkyl, $-OR^3$, $-COR^3$, $-CO_2R^3$, $-CONR^3R^4$, $-SO_2NR^3R^4$, $-SO_2R^3$, $-NCOR^3R^4$, $-NSO_2R^3R^4 -NR^3R^4$, $-(CR^3R^4)_m NR^8R^9$, $-(CR^3R^4)_m OR^8$, $-(CR^3R^4)_m$-aryl, $-(CR^3R^4)_m$-heteroaryl, $-T(CH_2)_mQR$, $-C(O)T(CH_2)_m QR^3$, or $-NR^3C(O)T(CH_2)_m QR^4$, $-CR^3=CR^4C(O)R^8$, or $-SR^4$;

E is C or N, provided that $R^7$ is absent when E is N; and $R^7$ is hydrogen, halogen, lower alkyl, lower alkoxy, or alkylcarbonyl;

Y is N or $CR^5$;

X and Z are independently hydrogen, halogen, lower alkyl, lower alkoxy, trifluoromethyl, hydroxy, nitrile, nitro, $-NR^3R^4$, $-N(O)R^3R^4$, $-SR^3$, $-C(O)R^3$, $-CO_2R^3$, $-CONR^3R^4$, $-SO_2NR^3R^4$, $SO_2R^3$, $-T(CH_2)_mQR^3$, $-C(O)T(CH_2)_mQR^3$, or $-NR^3C(O)T(CH_2)_mQR^4$;

m is 0–6;

T is O, S, $NR^3$, $N(O)R^3$, or $CR^3R^4$;

Q is O, S, $NR^3$, $N(O)R^3$, or $CO_2$;

$R^5$ is $NR^3R^4$, $N(O)R^3R^4$, OH, $OR^3$, $SR^3$, halo, $COR^3$, $(CH_2)_mR^3$, $CO_2R^3$, $CONR^3R^4$, $S(O)_nR^3$, $SO_2R^3$, $SO_2NR^3R^4$, $NR^3SO_2R^4$, nitrile, nitro, alkyl, alkoxyalkyl, $T(CH_2)_mQR^3$, $C(O)T(CH_2)_mQR^3$, $NR^3C(O)T(CH_2)_mQR^4$, or $T(CH_2)_mCO_2R^3$;

n is 0–2;

Each of $R^3$ and $R^4$ are independently hydrogen, lower alkyl, lower alkenyl, lower alkynyl, $(CH_2)_mAr$, arylalkyl, aryl, heteroarylalkyl, cycloalkyl, heterocyclic containing 5–10-membered rings containing at least one and up to three heteroatoms selected from nitrogen, oxygen, or sulfur, or heteroaryl containing one or more aromatic ring systems of 5- or 6-membered rings containing at least one and up to four heteroatoms selected from nitrogen, oxygen, or sulfur, or $R^3$ and $R^4$ together with the nitrogen to which they are attached form a cycloalkyl ring containing 3–8 members, up to four of which members are optionally carbonyl groups or heteroatoms independently selected from oxygen, sulfur, $S(O)$, $S(O)_2$, and nitrogen, wherein the carbocyclic group is unsubstituted or substituted with one, two, three, or four groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, mono- or dialkylamino, N-hydroxyacetamido, aryl, heteroaryl, carboxyalkyl, $-NR^8SO_2R^9$, $-C(O)NR^8R^9$, $-NR^8C(O)R^9$, $-C(O)OR^8$, $-(CH_2)_mS(O)_nR^8$, $-(CH_2)_m$-heteroaryl, $-O(CH_2)_m$-heteroaryl, $-(CH_2)_mC(O)NR^8R^9$, and $-O(CH_2)_mC(O)OR^8$; and Each of $R^8$ and $R^9$ are independently hydrogen, lower alkyl, lower alkenyl, lower alkynyl, $(CH_2)_mAr$, arylalkyl, aryl, heteroarylalkyl, cycloalkyl, heterocyclic containing 5–10-membered rings containing at least one and up to three heteroatoms selected from nitrogen, oxygen, or sulfur, or heteroaryl containing one or more aromatic ring systems of 5- or 6-membered rings containing at least one and up to four heteroatoms selected from nitrogen, oxygen, or sulfur.

4. A compound of the Formula IV

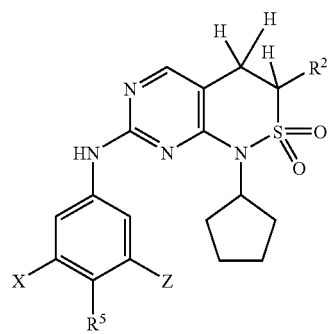

wherein:
$R^2$ is hydrogen, lower alkyl, lower hydroxyalkyl, lower alkoxy, halogen or acetyl,
X and Z independently are hydrogen or halo;
$R^5$ is $NR^3R^4$;
$R^3$ and $R^4$ taken together with the nitrogen to which they are attached form a 5- or 6-membered cycloalkyl ring, optionally containing an oxygen, nitrogen, or sulfur heteroatom, and optionally substituted with alkyl or substituted alkyl groups; or
a pharmaceutically acceptable salt thereof.

5. A compound of the Formula V

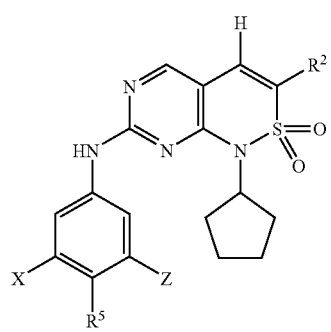

wherein:
$R^2$ is hydrogen, lower alkyl, lower alkyl alcohol, lower alkoxy, halogen or acetyl;
X and Z independently are hydrogen or halo;
$R^5$ is $NR^3R^4$;
$R^3$ and $R^4$ taken together with the nitrogen to which they are attached form a 5- or 6-membered cycloalkyl ring, optionally containing an oxygen, nitrogen, or sulfur heteroatom, and optionally substituted with alkyl or substituted alkyl groups; or
a pharmaceutically acceptable salt thereof.

6. A compound selected from the group consisting of:
1-Cyclopentyl-7-methylsulfanyl-1H-2-thia-1,6,8-triaza-naphthalene 2,2-dioxide (Compound 1;
1-Cyclopentyl-7-methanesulfinyl-1H-thia-1,6,8-triaza-naphthalene 2,2-dioxide (Compound 2);
4-[4-(1-Cyclopentyl-2,2-dioxo-1,2-dihydro-2l$^6$-thia-1,6,8-triaza-naphthalen-7-ylamino)-phenyl]-piperazine-1-carboxylic acid tert-butyl ester (Compound 3);
(1-Cyclopentyl-2,2-dioxo-1,2-dihydro-2l$^6$-thia-1,6,8-triaza-naphthalen-7-yl)-(4-piperazin-1-yl-phenyl)-amine (Compound 4);
4-[4-(1-Cyclopentyl-2,2-dioxo-1,2-dihydro-2l$^6$-thia-1,6,8-triaza-naphthalen-7-ylamino)-phenyl]2,2-dimethyl-piperazine-1-carboxylic acid tert-butyl ester (Compound 5);
(1-Cyclopentyl-2,2-dioxo-1,2-dihydro-2l$^6$-thia-1,6,8-triaza-naphthalen-7-yl)-[4-(3,3-dimethyl-piperazin-1-yl)-phenyl]-amine (Compound 6);
1-Cyclopentyl-3-methyl-7-methylsulfanyl-1H-2-thia-1,6,8-triaza-naphthalene 2,2-dioxide (Compound 7);
1-Cyclopentyl-7-methylsulfinyl-3-methyl-1H-2-thia-1,6,8-triaza-naphthalene 2,2-dioxide (Compound 8);
4-[4-(1-Cyclopentyl-3-methyl-2,2-dioxo-1,2-dihydro-2l$^6$-thia-1,6,8-triaza-naphthalen-7-ylamino)-phenyl]-piperazine-1-carboxylic acid tert-butyl ester (Compound 9);
(1-Cyclopentyl-3-methyl-2,2-dioxo-1,2-dihydro-2l$^6$-thia-1,6,8-triaza-naphthalen-7-yl)-(4-piperazin-1-yl-phenyl)-amine (Compound 10);
1-Cyclopentyl-3-ethyl-7-methylsulfanyl-1H-2-thia-1,6,8-triaza-naphthalene 2,2-dioxide (Compound 11);
1-Cyclopentyl-3-ethyl-7-methanesulfinyl-1H-2-thia-1,6,8-triaza-naphthalene 2,2-dioxide (Compound 12);
4-[4-(1-Cyclopentyl-3-ethyl-2,2-dioxo-1,2-dihydro-2l$^6$-thia-1,6,8-triaza-naphthalen-7-ylamino)-phenyl]-piperazine-1-carboxylic acid tert-butyl ester (Compound 13);

(1-Cyclopentyl-3-ethyl-2,2-dioxo-1,2-dihydro-2$l^6$-thia-1,6,8-triaza-naphthalen-7-yl)-(4-piperazin-1-yl-phenyl)-amine (Compound 14);

4-[4-(1-Cyclopentyl-2,2-dioxo-1,2,3,4-tetrahydro-2$l^6$-thia-1,6,8-triaza-naphthalen-7-ylamino)-phenyl]-piperazine-1-carboxylic acid tert-butyl ester (Compound 15);

(1-Cyclopentyl-2,2-dioxo-1,2,3,4-tetrahydro-2$l^6$-thia-1,6,8-triaza-naphthalen-7-yl)-(4-piperazin-1-yl-phenyl)-amine (Compound 16);

1-Ethyl-3-methyl-7-methylsulfanyl-1H-2-thia-1,6,8-triaza-naphthalene 2,2-dioxide (Compound 17);

1-Ethyl-7-methylsulfinyl-3-methyl-1H-2-thia-1,6,8-triaza-naphthalene 2,2-dioxide (Compound 18);

4-[4-(1-Ethyl-3-methyl-2,2-dioxo-1,2-dihydro-2$l^6$-thia-1,6,8-triaza-naphthalen-7-ylamino)-phenyl]-piperazine-1-carboxylic acid tert-butyl ester (Compound 19);

(1-Ethyl-3-methyl-2,2-dioxo-1,2-dihydro-2$l^6$-thia-1,6,8-triaza-naphthalen-7-yl)-(4-piperazin-1-yl-phenyl)-amine (Compound 20);

(1-Cyclopentyl-2,2-dioxo-1,2-dihydro-2$l^6$-thia-1,6,8-triaza-naphthalen-7-yl)-[4-(3,5-dimethyl-piperazin-1-yl)-phenyl]-amine (Compound 21);

(1-Isopropyl-2,2-dioxo-1,2-dihydro-2$l^6$-thia-1,6,8-triaza-naphthalen-7-yl)-(4-piperazin-1-yl-phenyl)-amine (Compound 22);

(1-Cyclopentyl-4-methyl-2,2-dioxo-1,2-dihydro-2$l^6$-thia-1,6,8-triaza-naphthalen-7-yl)-(4-piperazin-1-yl-phenyl)-amine (Compound 23);

(3-Bromo-1-cyclopentyl-2,2-dioxo-1,2-dihydro-2$l^6$-thia-1,6,8-triaza-naphthalen-7-yl)-(4-piperazin-1-yl-phenyl)-amine (Compound 24);

[4-(3-Amino-cyclopentyl)phenyl](1-cyclopentyl-2,2-dioxo-1,2-dihydro-2$l^6$-thia-1,6,8-triaza-naphthalen-7-yl)-amine (Compound 25);

(3-Chloro-4-piperazin-1-yl)-(1-cyclopentyl-2,2-dioxo-1,2-dihydro-2$l^6$-thia-1,6,8-triaza-naphthalen-7-yl)-amine (Compound 26);

(1-Cyclopentyl-2,2-dioxo-1,2-dihydro-2$l^6$-thia-1,6,8-triaza-naphthalen-7-yl)-(4-morpholin-4-yl-phenyl)-amine (Compound 27);

(1-Cyclopentyl-2,2-dioxo-1,2-dihydro-2$l^6$-thia-1,6,8-triaza-naphthalen-7-yl)-(5-piperazin-1-yl-pyridin-2-yl)-amine (Compound 28);

(1-Cyclohexyl-2,2-dioxo-1,2-dihydro-2$l^6$-thia-1,6,8-triaza-naphthalen-7-yl)-[4-(3,3-dimethyl-piperazin-1-yl)-phenyl]-amine (Compound 29);

(3-Bromo-1-cyclopentyl-2,2-dioxo-1,2-dihydro-2$l^6$-thia-1,6,8-triaza-naphthalen-7-yl)-[4-(3,5-dimethyl-piperazin-1-yl-phenyl)-amine (Compound 30);

(1-Isopropyl-3-methyl-2,2-dioxo-1,2-dihydro-2$l^6$-thia-1,6,8-triaza-naphthalen-7-yl)-(4-piperazin-1-yl-phenyl)-amine (Compound 31);

(1-Cyclopentyl-2,2-dioxo-1,2-dihydro-2$l^6$-thia-1,6,8-triaza-naphthalen-7-yl)-[4-(3,3-dimethyl-piperazin-1-yl)-phenyl]-amine (Compound 32);

(1-Cyclopentyl-2,2-dioxo-1,2,3,4-tetrahydro-2$l^6$-thia-1,6,8-triaza-naphthalen-7-yl)-(4-piperazin-1-yl-phenyl)-amine (Compound 33);

[1-Cyclopentyl-2,2-dioxo-7-(4-piperazin-1-yl-phenylamino 1,2-dihydro-2$l^6$-thia-1,6,8-triaza-naphthalen-3-yl]-methanol (Compound 34);

(1-Cyclohexyl-2,2-dioxo-1,2,3,4-tetrahydro-2$l^6$-thia-1,6,8-triaza-naphthalen-7-yl)-[4-(3,3-dimethyl-piperazin-1-yl)-phenyl]-amine (Compound 35);

(1-Cyclopentyl-2,2-dioxo-1,2,3,4-tetrahydro-2$l^6$-thia-1,6,8-triaza-naphthalen-7-yl)-[4-(3,5-dimethyl-piperazin-1-yl)-phenyl]-amine (Compound 36); and (1-Isopropyl-3-methyl-2,2-dioxo-1,2,3,4-tetrahydro-2$l^6$-thia-1,6,8-triazanaphthalen-7-yl)-(4-piperazin-1-yl-phenyl)-amine (Compound 37).

7. (1-Cyclopentyl-2,2-dioxo-1,2-dihydro-2$l^6$-thia-1,6,8-triaza-naphthalen-7-yl)-(4-piperazin-1-yl-phenyl)-amine (Compound 4).

* * * * *